(12) United States Patent
Shyjan et al.

(10) Patent No.: US 6,723,498 B1
(45) Date of Patent: Apr. 20, 2004

(54) CHK1 AND USES THEREOF

(75) Inventors: Andrew W. Shyjan, Nahant, MA (US); Mark Williamson, Saugus, MA (US); Shengfang Jin, West Roxbury, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/340,264

(22) Filed: Jun. 30, 1999

(51) Int. Cl.$^7$ .............................. C12Q 1/00; C12Q 1/68; G01N 33/567; G01N 33/574; G01N 33/48
(52) U.S. Cl. .............................. 435/4; 424/9.1; 424/9.2; 435/325; 435/6; 435/7.21; 435/7.23; 436/63; 436/64; 530/300; 530/350; 530/1.11; 530/18.7; 530/22.1; 530/23.1; 530/23.5
(58) Field of Search ................................ 435/4, 325, 6, 435/7.21, 7.23; 424/9.1, 9.2; 436/63, 64; 530/300, 350; 536/1.11, 18.7, 22.1, 23.1, 23.5

(56) References Cited

FOREIGN PATENT DOCUMENTS

| WO | WO 99/11795 | * | 3/1999 |

OTHER PUBLICATIONS

Chen et al., "Association of Chk1 with 14–3–3 proteins is stimulated by DNA damage" Genes Development 13:675–685, 1999.

Peng et al., "Mitotic and $G_2$ checkpoint control: Regulation of 14–3–3 protein binding by phosphorylation . . . " Science 277:1501–1505, 1997.

Sanchez et al., "Conservation of the Chk1 checkpoint pathway in mammals: Linkage of DNA Damage . . . " Science 277:1497–1500, 1997.

GenBank Accession No. AF016582, Sanchez et al., Sep. 9, 1997.

* cited by examiner

Primary Examiner—Alana M. Harris
(74) Attorney, Agent, or Firm—Millennium Pharmaceuticals, Inc.

(57) ABSTRACT

Increased expression of Chk1 is associated with drug resistance of certain cells (e.g., cancer cells). The invention provides methods for identifying drug resistant cells by measuring the expression or activity of Chk1, methods for identifying modulators of drug resistance, and methods for modulating drug resistance by modulating the expression or activity of Chk1.

38 Claims, 5 Drawing Sheets

```
   1 ggccggacag tccgccgagg tgctcggtgg agtcatggca gtgcccttttg tggaagactg
  61 ggacttggtg caaaccctgg gagaaggtgc ctatggagaa gttcaacttg ctgtgaatag
 121 agtaactgaa gaagcagtcg cagtgaagat tgtagatatg aagcgtgccg tagactgtcc
 181 agaaatatt aagaaagaga tctgtatcaa taaaatgcta aatcatgaaa atgtagtaaa
 241 attctatgt cacaggagag aaggcaatat ccaatattta ttcctggagt actgtagtgg
 301 aggagagctt tttgacagaa tagagccaga cataggcatg cctgaaccag atgctcagag
 361 attcttccat caactcatgg caggggtggt ttatctgcat ggtattggaa taactcacag
 421 ggatattaaa ccagaaaatc ttctgttgga tgaaagggat aacctcaaaa tctcagactt
 481 tggcttggca acagtattc ggtataataa tcgtgagcgt ttgttgaaca agatgtgtgg
 541 tactttacca tatgttgctc cagaacttct gaagagaaga gaatttcatg cagaaccagt
 601 tgatgttttgg tcctgtggaa tagtacttac tgcaatgctc gctggagaat tgccatggga
 661 ccaacccagt gacagctgtc aggagtattc tgactggaaa gaaaaaaaaa cataccctcaa
 721 cccttgaaa gacagcgatt ctgctcctct agctctgctg cataaaatct tagttgagaa
 781 tccatcagca agaattacca ttccagacat caaaaaagat agatggtaca acaaacccct
 841 caagaaaggg gcaaaaaggc cccgagtcac ttcaggtggt gtgtcagagt ctcccagtgg
 901 attttctaag cacattcaat ccaatttgga cttctctcca gtaaacagtg cttctagtga
 961 agaaaatgtg aagtactcca gttctcagcc agaaccccgc acaggtcttt ccttatggga
1021 taccagcccc tcatacattg ataaattggt acaagggatc agcttttccc agccacatg
1081 tcctgatcat atgcttttga atagtcagtt acttggcacc ccaggatcct cacagaaccc
1141 ctggcagcgg ttggtcaaaa gaatgacacg attctttacc aaattggatg cagacaaatc
1201 ttatcaatgc ctgaaagaga cttgtgagaa gttggctat caatggaaga aagttgtat
1261 gaatcaggtt actatatcaa caactgatag gagaaacaat aaactcattt tcaaagtgaa
1321 tttgttagaa atggatgata aaatattggt tgacttccgg ctttctaagg gtgatggatt
1381 ggagttcaag agacacttcc tgaagattaa agggaagctg attgatattg tgagcagcca
1441 gaaggttttgg cttcctgcca catgatcgga ccatcggctc tggggaatcc tggtgaatat
1501 agtgctgcta tgttgacatt attcttccta gagaagatta tcctgtcctg caaactgcaa
1561 atagtagttc ctgaagtgtt cacttccctg tttatccaaa catcttccaa tttattttgt
1621 ttgttcggca tacaaataat acctatatct taattgtaag caaaactttg gggaaaggat
1681 gaatagaatt catttgatta tttcttcatg tgtgtttagt atctgaattt gaaactcatc
1741 tggtggaaac caagtttcag gggacatgag ttttccagct tttatacaca cgtatctcat
1801 ttttatcaaa acattttgtt t
```

FIG. 1

MAVPFVEDWDLVQTLGEGAYGEVQLAVNRVTEEAVAVKIVDMKR
AVDCPENIKKEICINKMLNHENVVKFYGHRREGNIQYLFLEYCS
GGELFDRIEPDIGMPEPDAQRFFHQLMAGVVYLHGIGITHRDIK
PENLLLDERDNLKISDFGLATVFRYNNRERLLNKMCGTLPYVAP
ELLKRREFHAEPVDVWSCGIVLTAMLAGELPWDQPSDSCQEYSD
WKEKKTYLNPWKKIDSAPLALLHKILVENPSARITIPDIKKDRW
YNKPLKKGAKRPRVTSGGVSESPSGFSKHIQSNLDFSPVNSASS
EENVKYSSSQPEPRTGLSLWDTSPSYIDKLVQGISFSQPTCPDH
MLLNSQLLGTPGSSQNPWQRLVKRMTRFFTKLDADKSYQCLKET
CEKLGYQWKKSCMNQVTISTTDRRNNKLIFKVNLLEMDDKILVD
FRLSKGDGLEFKRHFLKIKGKLIDIVSSQKVWLPAT

FIG. 2

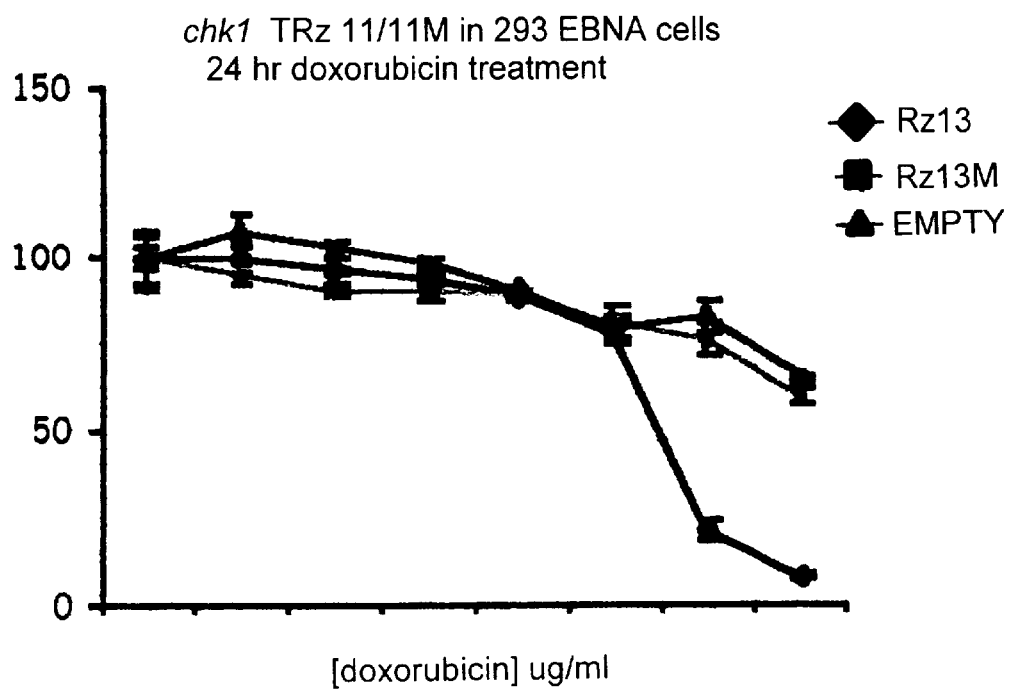

FIG. 5

CHK1 AND USES THEREOF

BACKGROUND OF THE INVENTION

The invention relates to chemotherapy and drug resistance.

Cancer chemotherapy commonly involves the administration of one or more cytotoxic or cytostatic drugs to a patient. The goal of chemotherapy is to eradicate a substantially clonal population (tumor) of transformed cells from the body of the individual, or to suppress or to attenuate growth of the tumor. Tumors may occur in solid or liquid form, the latter comprising a cell suspension in blood or other body fluid. A secondary goal of chemotherapy is stabilization (clinical management) of the afflicted individual's health status. Although the tumor may initially respond to chemotherapy, in many instances the initial chemotherapeutic treatment regimen becomes less effective or ceases to impede tumor growth. The selection pressure induced by chemotherapy promotes the development of phenotypic changes that allow tumor cells to resist the cytotoxic effects of a chemotherapeutic drug. Often, exposure to one drug induces resistance to that drug as well as other drugs to which the cells have not been exposed.

Cell cycle checkpoints are regulatory systems that control the order and timing of certain events in the cell cycle. These checkpoints are important for ensuring that cells divide properly. For example, DNA damage leads to activation of a cell cycle checkpoint regulatory system that arrests the cell cycle and activates genes involved in repair of DNA damage. This system prevents progression of the cell cycle until the DNA damage has been repaired.

Chk1, a kinase, is thought to be involved in the DNA damage cell cycle checkpoint. Chk1 is thought to participate in the phosphorylation of Cdc25 in response to DNA damage. Phosphorylation of Cdc25 prevents activation of the Cdc2-cyclin B complex thereby blocking mitotic entry.

SUMMARY OF THE INVENTION

The present invention concerns checkpoint kinase 1 (Chk1; Genbank Accession No. AF016582; Sanchez et al. (1997) *Science* 277:1497). Applicants have found that expression of Chk1 is up regulated in certain vinblastin resistant cancer cell lines and in certain adromycin resistant cancer cell lines. Applicants have also found that a ribozyme designed to decrease Chk1 expression can increase drug sensitivity.

Chk1 nucleic acids and polypeptides are useful in diagnostic methods related to identification of drug resistant cells (e.g., cancer cells). Chk1 nucleic acids and polypeptides are also useful in screening methods directed to the identification of compounds that can modulated (increase or decrease) the drug resistance of a particular cell type or multiple cell types.

The invention includes a method for detecting the presence of a Chk1 polypeptide in a sample, e.g., a biological sample. This method features the steps of contacting the sample with a compound which selectively binds to the polypeptide and then determining whether the compound binds to a polypeptide in the sample. In some cases, the compound which binds to the polypeptide is an antibody.

The invention also features methods for detecting the presence of a Chk1 nucleic acid molecule in a sample. This method includes the steps of contacting the sample with a nucleic acid probe or primer which selectively hybridizes to a Chk1 nucleic acid molecule (e.g., an mRNA encoding Chk1); and then determining whether the nucleic acid probe or primer binds to a nucleic acid molecule in the sample.

Also within the invention are kits that include a compound which selectively binds to a Chk1 polypeptide or nucleic acid and instructions for use. Such kits can be used to determine whether cells within a biological sample, e.g., a sample of patient cells, are drug resistant.

The invention features methods for identifying a compound which binds to a Chk1 polypeptide. These methods include the steps of contacting a Chk1 polypeptide with a test compound and then determining whether the polypeptide binds to the test compound. In various embodiments of these methods, the binding of the test compound to the Chk1 polypeptide is detected using an assay which measures binding of the test compound to the polypeptide or using a competition binding assay.

The invention also includes a method for modulating the activity of a Chk1 polypeptide. This method includes the steps of contacting the polypeptide or a cell expressing the polypeptide with a compound which binds to the polypeptide in a sufficient concentration to modulate the activity of the polypeptide.

In another aspect, the invention provides a method for identifying a compound that modulates the activity of a Chk1 polypeptide (e.g., a Chk1 protein). In general, such methods entail measuring a biological activity of the polypeptide in the presence and absence of a test compound and identifying those compounds which alter the activity of the polypeptide (e.g., alter the ability of Chk1 to phosphorylated Cdc25). One such method includes the steps of contacting the polypeptide with a test compound and then determining the effect of the test compound on the activity of the polypeptide to thereby identify a compound which modulates the activity of the polypeptide.

The invention also features methods for identifying a compound which modulates the expression of a Chk1 nucleic acid or a Chk1 polypeptide by measuring the expression of the nucleic acid or polypeptide in the presence and absence of a compound.

Other aspects of the invention are methods and compositions relating to drug resistance. A "drug-resistant phenotype" refers to a cellular phenotype which is associated with increased survival (compared to a less drug-resistant cell) after exposure to a particular dose of a drug, e.g., a chemotherapeutic drug, compared to a cell that does not have this phenotype. A "drug-resistant cell" refers to a cell that exhibits this phenotype. Drug resistance can be characterized by lower intracellular concentration of a drug compared to a non-resistant cell or a less resistant cell as well as altered ability of a drug to affect its target compared to a non-resistant cell or a less resistant cell. Drug resistance is described in detail by Hochhauser and Harris ((1991) *Brit. Med. Bull.* 47:178–96); Simon and Schindler ((1994) *Proc. Nat'l Acad Sci USA* 91: 3497–504); and Harris and Hochhauser ((1992) *Acta Oncologica* 31:205–213); Scotto et al. ((1986) *Science* 232: 751–55). Multi-drug resistance can be associated with, for example, altered composition of plasma membrane phospholipids; increased drug binding and intracellular accumulation; altered expression or activity of plasma membrane or endomembrane channels, transporters or translocators; altered rates of endocytosis and associated alteration in targeting of endosomes; altered exocytosis; altered intracellular ionic environments; altered expression or activity of proteins involved in drug detoxification; and altered expression or activity of proteins involved in DNA repair or replication.

Also within the invention is a method of determining whether a cell has a drug-resistant phenotype by measuring the expression (or activity) of Chk1 in the cell and comparing this expression to that in a control cell. Increased expression (or activity) of Chk1 in the cell compared to the control cell indicates that the cell has a drug-resistant phenotype. In one embodiment of this method, Chk1 expression is determined by measuring Chk1 protein (e.g., measuring Chk1 protein using an antibody directed against Chk1). In another embodiment, Chk1 expression is measured by quantifying mRNA encoding Chk1 or the copy number of the Chk1 gene. In another embodiment Chk1 activity is measured using any assay which can quantify a biological activity of Chk1.

The invention also includes a method for modulating the drug resistance of a cell by modulating Chk1 expression or activity within the cell. Thus, in one embodiment, the drug-resistance of a cell is reduced by contacting the cell with a molecule (e.g., an antisense nucleic acid molecule) that reduces the expression of Chk1 within the cell.

Another aspect of the present invention is a method of improving effectiveness of chemotherapy for a mammal having a disorder associated with the presence of drug-resistant neoplastic cells. In this method, a chemotherapeutic drug and a molecule that reduces expression of Chk1 can be co-administered to a mammal. Alternatively, the chemotherapeutic drug can be administered before or after administration of the compound that reduces expression of Chk1.

The invention also includes a method of identifying a compound that modulates the drug resistance of a cell by first contacting the cell with a test compound and then measuring and comparing Chk1 expression in the cell exposed to the compound to Chk1 expression in a control cell not exposed to the compound. The compound is identified as modulator of drug resistance when the level of Chk1 expression in the cell exposed to the compound differs from the level of Chk1 expression in cells not exposed to the compound. In one embodiment of this method, the cell has a drug-resistant phenotype. In another embodiment, the cell is a mammalian cell. This method may also include an optional step of measuring the drug resistance of the cell in the presence of the identified modulator of drug resistance. The Chk1 modulating compounds that are identified in the foregoing methods are also included within the invention.

The invention also features a method of treating a mammal suspected of having a disorder associated with the presence of drug-resistant cells. This method includes the steps of determining whether a mammal has a disorder associated with the presence of drug-resistant cells having increased Chk1 expression (e.g., drug-resistant cancer), and administering to the mammal a compound that sufficiently reduces the expression of Chk1 so that the drug resistance of the cells associated with the disorder is modulated (i.e., reduced).

Another feature of the invention is a method for treating a patient having a neoplastic disorder (e.g., cancer) by administering to the patient a therapeutically effective amount of a compound that decreases the expression of Chk1.

In the context of cancer treatment, the expression level of Chk1 may be used to: 1) determine if a cancer can be treated by an agent or combination of agents; 2) determine if a cancer is responding to treatment with an agent or combination of agents; 3) select an appropriate agent or combination of agents for treating a cancer; 4) monitor the effectiveness of an ongoing treatment; and 5) identify new cancer treatments (either single agent or combination of agents). In particular, Chk1 may be used as a marker (surrogate and/or direct) to determine appropriate therapy, to monitor clinical therapy and human trials of a drug being tested for efficacy and in developing new agents and therapeutic combinations.

Accordingly, the present invention provides methods for determining whether an agent, e.g., a chemotherapeutic agent such as vinblastin, will be effective in reducing the growth rate of cancer cells comprising the steps of: a) obtaining a sample of cancer cells; b) determining the level of expression in the cancer cells of Chk1; and c) identifying that an agent will be effective when Chk1 is not expressed or is expressed at relatively low level. Alternatively, in step (c), an agent can be identified as being relatively ineffective when to use to treat the cancer when Chk1 is expressed or is expressed at relatively high level.

As used herein, an agent is said to reduce the rate of growth of cancer cells when the agent can reduce at least 50%, preferably at least 75%, most preferably at least 95% of the growth of the cancer cells at a given concentration of the agent. Such inhibition can further include a reduction in survivability and an increase in the rate of death of the cancer cells. The amount of agent used for this determination will vary based on the agent selected. Typically, the amount will be a predefined therapeutic amount.

As used herein, an agent is defined broadly as anything that cancer cells can be exposed to in a therapeutic protocol. In the context of the present invention, such agents include, but are not limited to, chemotherapeutic agents, such as anti-metabolic agents, e.g., Ara AC, 5-FU and methotrexate, antimitotic agents, e.g., taxol, vinblastine and vincristine, alkylating agents, e.g., melphanlan, BCNU and nitrogen mustard, Topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light. A preferred agents is doxorubicin.

The agents tested in the present methods can be a single agent or a combination of agents. For example, the present methods can be used to determine whether a single chemotherapeutic agent, such as methotrexate, can be used to treat a cancer or whether a combination of two or more agents can be used.

Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkins disease; and tumors of the nervous system including glioma, meningoma, medulloblastoma, schwannoma or epidymoma.

The source of the cancer cells used in the methods of the invention will be based on how the method of the present invention is being used. For example, if the method is being used to determine whether a patient's cancer can be treated with an agent, or a combination of agents, then the preferred source of cancer cells will be cancer cells obtained from a cancer biopsy from the patient. Alternatively, cancer cells line of similar type to that being treated can be assayed. For example if breast cancer is being treated, then a breast cancer cell line can be used. If the method is being used to monitor the effectiveness of a therapeutic protocol, then a tissue sample from the patient being treated is the preferred source. If the method is being used to identify new therapeutic agents or combinations, then any cancer cells, e.g., cells of a cancer cell line, can be used.

A skilled artisan can readily select and obtain the appropriate cancer cells that are used in the present method. For cancer cell lines, sources such as The National Cancer Institute, for the NCI-60 cells used in the examples, are preferred. For cancer cells obtained from a patient, standard biopsy methods, such as a needle biopsy, can be employed.

In the methods of the present invention, the level or amount of expression of Chk1 is determined. As used herein, the level or amount of expression refers to the absolute level of expression of an mRNA encoded by the gene or the absolute level of expression of the protein encoded by the gene (i.e., whether or not expression is or is not occurring in the cancer cells).

As an alternative to making determinations based on the absolute expression level of selected genes, determinations may be based on the normalized expression levels. Expression levels are normalized by correcting the absolute expression level of a sensitivity or resistance gene by comparing its expression to the expression of a gene that is not a sensitivity or resistance gene, e.g., a housekeeping genes that is constitutively expressed. Suitable genes for normalization include housekeeping genes such as the acting gene. This normalization allows one to compare the expression level in one sample, e.g., a patient sample, to another sample, e.g., a non-cancer sample, or between samples from different sources. Alternatively, the expression level can be provided as a relative expression level. To determine a relative expression level of a gene, the level of expression of the gene is determined for 10 or more samples, preferably 50 or more samples, prior to the determination of the expression level for the sample in question. The mean expression level of each of the gene assayed in the larger number of samples is determined and this is used as a baseline expression level for the gene in question. The expression level of the gene determined for the test sample (absolute level of expression) is then divided by the mean expression value obtained for that gene. This provides a relative expression level and aids in identifying extreme cases of sensitivity or resistance. Preferably, the samples used will be from similar tumors or from non-cancerous cells of the same tissue origin as the tumor in question. The choice of the cell source is dependent on the use of the relative expression level data. For example, using tumors of similar types for obtaining a mean expression score allows for the identification of extreme cases of sensitivity or resistance. Using expression found in normal tissues as a mean expression score aids in validating whether the gene assayed is tumor specific (versus normal cells).

Also within the invention is a method for increasing drug resistance in a cell having an undesirably low level of Chk1 expression by administering a compound that increases the expression of Chk1. Such methods are useful for the protection of non-neoplastic cells during chemotherapy.

The invention features a method for determining whether a test compound modulates the drug resistance of a cell, the method including: a) determining the level of Chk1 expression (e.g., Chk1 encoded by an endogenous or heterologous gene) in a cell in the presence of a test compound; b) determining the level of Chk1 expression in the cell in the absence of the test compound; and c) identifying the compound as a modulator of drug resistance of the cell if the level of expression of Chk1 in the cell in the presence of the test compound differs from the level of expression of Chk1 in the cell in the absence of the test compound.

The invention features a method for determining whether a test compound modulates the drug resistance of a cell, the method including: a) determining the level of Chk1 activity in a cell in the presence of a test compound; b) determining the level of Chk1 activity in the cell in the absence of the test compound; and c) identifying the compound as a modulator of drug resistance of the cell if the level of activity of Chk1 in the cell in the presence of the test compound differs from the level of activity of Chk1 in the cell in the absence of the test compound.

The invention also features a method for determining whether a test compound modulates the drug resistance of a cell, the method including: a) incubating Chk1 protein in the presence of a test compound; b) determining whether the test compound binds to the Chk1 protein; c) selecting a test compound which binds to the Chk1 protein; d) administering the test compound selected in step c) to a non-human mammal having drug resistant cells; e) determining whether the test compound alters the drug resistance of the cells in the non-human mammal; and f) identifying the test compound as a modulator of drug resistance of the cell if the compound alters the drug resistance of the cells in step e).

The invention further features a method for determining whether a test cell has a drug-resistant phenotype, the method including: a) measuring the expression of Chk1 in the test cell; b) comparing the expression of Chk1 measured in step a) to the expression of Chk1 in a control cell not having a drug-resistant phenotype; and c) determining that the test cell has a drug resistant phenotype if the expression of Chk1 in the test cell is greater than the expression of Chk1 in the control cell.

In another aspect the invention features a method of determining whether a test cell has a drug-resistant phenotype, the method including: a) measuring the activity of Chk1 in the test cell; b) comparing the activity of Chk1 measured in step a) to the activity of Chk1 in a control cell not having a drug-resistant phenotype; and c) determining that the test cell has a drug resistant phenotype if the activity of Chk1 in the test cell is greater than the activity of Chk1 in the control cell.

In yet another aspect the invention features a method for determining whether a subject has or is at risk f developing a drug resistant tumor, the method including: a) measuring the expression of Chk1 mRNA in a biological sample obtained from the subject (using, e.g., a nucleic acid molecule that hybridizes to Chk1 mRNA); b) comparing the expression of Chk1 mRNA measured in step a) to the expression of Chk1 mRNA in a biological sample obtained from a control subject not having a drug resistant tumor; and c) determining that the patient has or is at risk of developing a drug resistant tumor if the expression of Chk1 mRNA in the biological sample obtained from the patient is higher than the expression of Chk1 mRNA in the biological sample obtained from the control subject.

In still another aspect the invention features a method for determining whether a subject has or is at risk of developing a drug resistant tumor, the method including: a) measuring the activity of Chk1 in a biological sample obtained from the subject (using, e.g., an agent that binds to Chk1 protein); b) comparing the activity of Chk1 measured in step a) to the activity of Chk1 in a biological sample obtained from a control subject not having a drug resistant tumor; and c) determining that the patient has or is at risk of developing a drug resistant tumor if the activity of Chk1 in the biological sample obtained from the patient is higher than the activity of Chk1 in the biological sample obtained from the control subject.

The invention also features a method for monitoring the effect of an anti-tumor treatment on a patient, the method including: a) measuring the expression of Chk1 in a tumor sample obtained from the patient (using, e.g., a nucleic acid molecule that hybridizes to Chk1 mRNA); b) comparing the expression of Chk1 measured in step a) to the expression of Chk1 in a control sample of cells; and c) determining that the anti-tumor treatment should be discontinued or modified if the expression of Chk1 in the tumor sample is higher than the expression of Chk1 in the control sample of cells.

The invention also features a method for monitoring the effect of an anti-tumor treatment on a patient, the method including: a) measuring the activity of Chk1 in a tumor sample obtained from the patient (using, e.g., an agent that binds to Chk1 protein); b) comparing the activity of Chk1 measured in step a) to the activity of Chk1 in a control sample of cells; and c) determining that the anti-tumor treatment should be discontinued or modified if the activity of Chk1 in the tumor sample is higher than the activity of Chk1 in the control sample of cells.

The invention further features a method for modulating the drug resistance of a cell by modulating Chk1 expression within the cell and a method for reducing the drug resistance of cell by contacting the cell with a molecule which reduces the expression of Chk1 within the cell.

The invention also features a method of increasing the effectiveness of a chemotherapeutic compound in a patient suffering from a disorder associated with the presence of drug-resistant neoplastic cells, the method including: a) administering a chemotherapeutic compound to the patient; and b) administering a compound with reduces Chk1 expression to the patient.

The invention features a method of treating a mammal suspected of having a disorder associated with the presence of drug-resistant cells, the method including administering to the mammal a compound that reduces the expression of Chk1 in the drug-resistant cells, the reduction be sufficient to reduce the drug resistance of the drug resistant cells and a method for increasing the drug resistance of cell that has an undesirably low level of Chk1 expression, the method including exposing the cell to a compound that increases the expression of Chk1.

The invention also features a method for treating a drug resistant tumor in a patient, the method comprising administering to said subject an amount of a Chk1 antagonist effective to reduce drug resistance of said tumor in the patient. In another aspect, the invention features the use of an inhibitor of Chk1 expression, or pharmaceutically acceptable salt thereof, or a pharmaceutical composition containing either entity, for the manufacture of a medicament for the treatment of a drug resistant tumor in a patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the detailed description and from the claims. Although materials and methods similar or equivalent to those described herein can be used in the practice or testing of the invention, the preferred materials and methods are described below.

BRIEF DESCRIPTION OF THE DRAWINGS

FIG. 1 depicts the nucleotide sequence (SEQ ID NO:1) of a cDNA encoding human Chk1 (GenBank Accession Number AF016582).

FIG. 2 depicts the predicted amino acid sequence (SEQ ID NO:2) of human Chk1 (GenBank Accession Number AF016582).

FIG. 5 depicts the results of an assay designed to measure the drug resistance of 293EBNA cells transfected with a ribozyme (Rz11; diamond), a mutant ribozyme (Rz11M; squares), or vector only (empty; triangles).

DETAILED DESCRIPTION OF THE INVENTION

Figure 3:
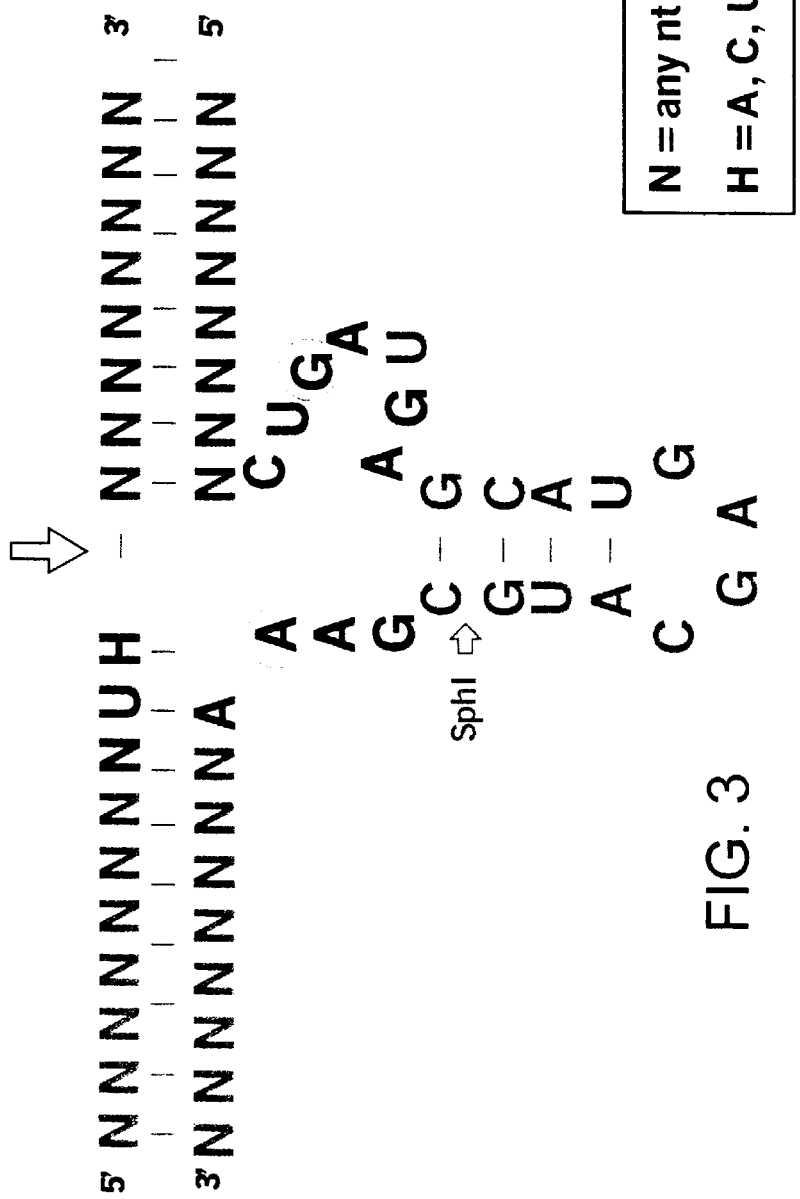
FIG. 3 depicts the structure of a hammerhead ribozyme (3' to 5' strand) base-paired with a RNA that is to be cleaved (5' to 3' strand).

The nucleotide sequence of a cDNA encoding a human Chk1 protein (SEQ ID NO:1) and the predicted amino acid sequence of human Chk1 protein (SEQ ID NO: 2) are shown in FIGS. 1 and 2 respectively.

The association between Chk1 expression and drug resistance was discovered during a search for genes that are more highly expressed in a drug resistant cell line than in the relatively drug sensitive cell line from which the drug resistant cell-line was derived.

The studies described below in Example 1 demonstrate that Chk1 is expressed at a higher level in certain cancers than in no-cancerous cells. The studies in Example 2 demonstrate that Chk1 is expressed at a higher level in certain drug resistant cell lines than in the less drug resistant cell lines from which the drug resistant cell lines were derived. Example 3 describes the preparation of purified human Chk1. The studies described in Example 4 provide evidence that decreasing the expression of Chk1 renders cells more sensitive to doxorubicin.

Various aspects of the invention are described in further detail in the following subsections.

I. Isolated Nucleic Acid Molecules

Isolated nucleic acid molecules that encode Chk1 proteins or biologically active portions thereof, as well as nucleic acid molecules sufficient for use as hybridization probes to identify Chk1-encoding nucleic acids (e.g., Chk1 mRNA) and fragments for use as PCR primers for the amplification or mutation of Chk1 nucleic acid molecules, are useful in the methods of the invention. Various methods for the preparation and use of Chk1 nucleic acid molecules are described below.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An isolated nucleic acid molecule is one which is separated from other nucleic acid molecules which are present in the natural source of the nucleic acid. Preferably, an isolated nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. An isolated Chk1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an isolated nucleic acid molecule, such as a CDNA molecule, can be substantially free of other cellular material, or culture medium when produced by recombinant techniques, or substantially free of chemical precursors or other chemicals when chemically synthesized.

A Chk1 nucleic acid molecule, e.g., a nucleic acid molecule having the nucleotide sequence of SEQ ID NO:1 or SEQ ID NO:3, or a complement thereof, can be isolated using standard molecular biology techniques and the sequence information provided herein. Chk1 nucleic acid molecules can be isolated using standard hybridization and cloning techniques (e.g., as described in Sambrook et al., eds., *Molecular Cloning: A Laboratory Manual*. 2nd, ed., Cold Spring Harbor Laboratory, Cold Spring Harbor Laboratory Press, Cold Spring Harbor, N.Y., 1989).

A Chk1 nucleic acid can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to Chk1 nucleotide sequences can be prepared by standard synthetic techniques, e.g., using an automated DNA synthesizer.

Useful Chk1 nucleic acid molecules can comprise only a portion of a nucleic acid sequence encoding Chk1, for example, a fragment which can be used as a probe or primer for identifying and/or quatifying Chk1 mRNA in a biological sample. A probe or primer can include at least about 12, 25, 50, 75, 100, 125, 150, 175, 200, 250, 300, 350 or 400 nucleotides and hybridizes, e.g., under stringent conditions, to a Chk1 mRNA, e.g, an mRNA comprising the nucleotide sequence of SEQ ID NO:1 or SEQ ID NO:3.

Probes based on the human Chk1 nucleotide sequence can be used to detect Chk1 transcripts or genomic sequences. The probe comprises a label group attached thereto, e.g., a radioisotope, a fluorescent compound, an enzyme, or an enzyme co-factor. Such probes can be used as a part of a diagnostic test kit for identifying cells or tissue which mis-express a Chk1 protein, such as by measuring a level of a Chk1-encoding nucleic acid in a sample of cells from a subject, e.g., detecting Chk1 mRNA levels or determining whether a genomic Chk1 gene has been mutated, deleted, or amplified.

A nucleic acid fragment encoding a "biologically active portion of Chk1 " can be prepared by isolating a portion of SEQ ID NO:3 which encodes a polypeptide having a Chk1 biological activity, expressing the encoded portion of Chk1 protein (e.g., by recombinant expression in vitro) and assessing the activity of the encoded portion of Chk1.

In addition to the probes and primers described above, isolated nucleic acid molecules of at least 50, 100, 200, 300, 325, 350, 375, 400, 425, 450, 500, 550, 600, 650, 700, 800, 900, 1000, 1200, 1400, 1600, or 1800 nucleotides that hybridize under stringent conditions to a nucleic acid molecule comprising the nucleotide sequence, preferably the coding sequence of SEQ ID NO:1 or SEQ ID NO:3 are useful in the methods of the invention.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in x sodium chloride/sodium citrate (SSC) at about 450° C., followed by one or more washes in 0.2×SSC, 0.1% SDS at 50 to 65° C.

Nucleic acid molecules encoding Chk1 proteins that contain changes in amino acid residues that are not essential for activity can be used in the methods of the invention. Such Chk1 proteins differ in amino acid sequence from SEQ ID NO:2 yet retain biological activity. For example, the isolated nucleic acid molecule may include a nucleotide sequence encoding a protein that includes an amino acid sequence that is at least about 45% identical, 65%, 75%, 85%, 95%, or 98% identical to the amino acid sequence of SEQ ID NO:2.

An isolated nucleic acid molecule encoding a Chk1 protein having a sequence which differs from that of SEQ ID NO:2 can be created by introducing one or more nucleotide substitutions, additions or deletions into the nucleotide sequence of SEQ ID NO:3 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Chk1 is preferably replaced with another amino acid residue from the same side chain family. Alternatively, mutations can be introduced randomly along all or part of a Chk1 coding sequence, such as by saturation mutagenesis, and the resultant mutants can be screened for Chk1 biological activity to identify mutants that retain activity. Following mutagenesis, the encoded protein can be expressed recombinantly and the activity of the protein can be determined.

Antisense molecules, i.e., molecules which are complementary to a sense nucleic acid encoding a protein, e.g., complementary to the coding strand of a double-stranded cDNA molecule or complementary to an mRNA sequence are useful in the methods of the invention, e.g., for reducing expression of Chk1 to reduce the drug resistance of a cell. The antisense nucleic acid can be complementary to an entire Chk1 coding strand, or to only a portion thereof, e.g., all or part of the protein coding region (or open reading frame). An antisense nucleic acid molecule can be antisense to a noncoding region of the coding strand of a nucleotide sequence encoding Chk1. The noncoding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, 50, or 100 nucleotides in length. An antisense Chk1 nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

An antisense nucleic acid molecule is typically administered to a subject or generated in situ such that they hybridize with or bind to cellular mRNA and/or genomic DNA encoding a Chk1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule can be an α-anomeric nucleic acid molecule. An α-anomeric nucleic acid molecule forms specific double-stranded hybrids with complementary RNA in which the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) FEDS Lett. 215:327–330).

Ribozymes, which are catalytic RNA molecules with ribonuclease activity which are capable of cleaving a single-stranded nucleic acid, such as an mRNA, to which they have a complementary region can be used in the methods of the invention. Thus, ribozymes (e.g., hammerhead ribozymes (described in Haselhoff and Gerlach (1988) *Nature* 334:585–591)) can be used to catalytically cleave Chk1 mRNA transcripts to thereby inhibit translation of Chk1 mRNA. A ribozyme having specificity for a Chk1-encoding nucleic acid can be designed based upon the nucleotide sequence of Chk1 (e.g., SEQ ID NO:1, SEQ ID NO:3). For example, a derivative of a Tetrahymena L-19 IVS RNA can be constructed in which the nucleotide sequence of the active site is complementary to the nucleotide sequence to be cleaved in a Chk1-encoding mRNA. See, e.g., Cech et al. U.S. Pat. No. 4,987,071; and Cech et al. U.S. Pat. No. 5,116,742. Alternatively, Chk1 mRNA can be used to select a catalytic RNA having a specific ribonuclease activity from a pool of RNA molecules. See, e.g., Bartel and Szostak (1993) *Science* 261:1411–1418.

Other useful nucleic acid molecules are those which form triple helical structures. For example, Chk1 gene expression can be inhibited by targeting nucleotide sequences complementary to the regulatory region of the Chk1 (e.g., the Chk1 promoter and/or enhancers) to form triple helical structures that prevent transcription of the Chk1 gene in target cells. See generally, Helene (1991) *Anticancer Drug Des.* 6(6): 569–84;. Helene (1992) Ann. N.Y. Acad. Sci. 660:27–36; and Maher (1992) *Bioassays* 14(12):807–15.

Nucleic acid molecules useful in the methods of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci. USA* 93: 14670–675.

PNAs of Chk1 can be used for therapeutic and diagnostic applications. For example, PNAs can be used as antisense or antigene agents for sequence-specific modulation of gene expression by, e.g., inducing transcription or translation arrest or inhibiting replication. PNAs of Chk1 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence analysis and hybridization (Hyrup (1996) supra; Perry-O'Keefe et al. (1996) *Proc. Natl. Acad. Sci. USA* 93:14670–675).

PNAs of Chk1 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of Chk1 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) *Nucleic Acids Research* 24(17):3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a linker between the PNA and the 5' end of DNA (Mag et al. (1989) *Nucleic Acid Res*. 17:5973–88). PNA monomers are then coupled in a stepwise manner to produce a chimeric molecule with a 5' PNA segment and a 3' DNA segment (Finn et al. (1996) *Nucleic Acids Research* 24(17):3357–63). Alternatively, chimeric molecules can be synthesized with a 5' DNA segment and a 3' PNA segment (Peterser et al. (1975) *Bioorganic Med. Chem. Lett.* 5:1119-11124).

Useful oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio/Techniques* 6:958–976) or intercalating agents (See, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated Chk1 Proteins and Anti-Chk1 Antibodies

Isolated Chk1 proteins, and biologically active portions thereof, as well as polypeptide fragments suitable for use as immunogens to raise anti-Chk1 antibodies are useful in the methods of the invention. Methods for the preparation and use of these molecules are described below. In general, Chk1 proteins can be isolated from cells or tissue sources by an appropriate purification scheme using standard protein purification techniques, produced by recombinant DNA techniques, or synthesized chemically using standard peptide synthesis techniques.

An "isolated" or "purified" protein or biologically active portion thereof is substantially free of cellular material or other contaminating proteins from the cell or tissue source from which the Chk1 protein is derived, or substantially free from chemical precursors or other chemicals when chemically synthesized. The language "substantially free of cellular material" includes preparations of Chk1 protein in which the protein is separated from cellular components of the cells from which it is isolated or recombinantly produced. Thus, Chk1 protein that is substantially free of cellular material includes preparations of Chk1 protein having less than about 30%, 20%, 10%, or 5% (by dry weight) of non-Chk1 protein (also referred to herein as a "contaminating protein"). When the Chk1 protein or biologically active portion thereof is recombinantly produced, it is also preferably substantially free of culture medium, i.e., culture medium represents less than about 20%, 10%, or 5% of the volume of the protein preparation. When Chk1 protein is produced by chemical synthesis, it is preferably substantially free of chemical precursors or other chemicals, i.e., it is separated from chemical precursors or other chemicals which are involved in the synthesis of the protein. Accordingly such preparations of Chk1 protein have less than about 30%, 20%, 10%, 5% (by dry weight) of chemical precursors or non-Chk1 chemicals.

Biologically active portions of a Chk1 protein include peptides comprising amino acid sequences sufficiently identical to or derived from the amino acid sequence of the Chk1 protein (e.g., the amino acid sequence shown in SEQ ID NO:2), which include less amino acids than the full length Chk1 proteins, and exhibit at least one activity of a Chk1 protein. Typically, biologically active portions comprise a domain or motif with at least one activity of the Chk1 protein. A biologically active portion of a Chk1 protein can be a polypeptide which is, for example, 10, 25, 50, 100, 200, 300, 400, or more amino acids in length.

Moreover, other biologically active portions, in which other regions of the protein are deleted, can be prepared by recombinant techniques and evaluated for one or more of the functional activities of a native Chk1 protein. A preferred Chk1 protein has the amino acid sequence of SEQ ID NO:2. Other useful Chk1 proteins are substantially identical to SEQ ID NO:2 and retain the functional activity of the protein of SEQ ID NO:2 yet differ in amino acid sequence due to natural allelic variation or mutagenesis. Accordingly, a useful Chk1 protein is a protein which includes an amino acid sequence at least about 45%, preferably 55%, 65%, 75%, 85%, 95%, or 99% identical to the amino acid sequence of SEQ ID NO:2 and retains the functional activity of the Chk1 proteins of SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Nat'l Acad. Sci. USA* 87:2264–2268, modified as in Karlin and Altschul (1993) *Proc. Nat'l Acad. Sci. USA* 90:5873–5877. Such an algorithm is incorporated into the NBLAST and XBLAST programs of Altschul, et al. (1990) *J MoL Biol.* 215:403–410. BLAST nucleotide searches can be performed with the NBLAST program, score=100, wordlength=12 to obtain nucleotide sequences homologous to Chk1 nucleic acid molecules of the invention. BLAST protein searches can be performed with the XBLAST program, score=50, wordlength=3 to obtain amino acid sequences homologous to Chk1 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See the National Institute of Health website at address: World Wide Web (www).ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used .

The percent identity between two sequences can be determined using techniques similar to those described above, with or without allowing gaps. In calculating percent identity, only exact matches are counted.

Chk1 chimeric or fusion proteins are also useful in the methods of the invention. As used herein, a Chk1 "chimeric protein" or "fusion protein" comprises a Chk1 polypeptide operatively linked to a non-Chk1 polypeptide. A "Chk1 polypeptide" refers to a polypeptide having an amino acid sequence corresponding to Chk1, whereas a "non-Chk1 polypeptide" refers to a polypeptide having an amino acid sequence corresponding to a protein which is not substantially identical to the Chk1 protein, e.g., a protein which is different from the Chk1 protein and which is derived from the same or a different organism. Within a Chk1 fusion protein the Chk1 polypeptide can correspond to all or a portion of a Chk1 protein, preferably at least one biologically active portion of a Chk1 protein. Within the fusion protein, the term "operatively linked" is intended to indicate that the Chk1 polypeptide and the non-Chk1 polypeptide are fused in-frame to each other. The non-Chk1 polypeptide can be fused to the N-terminus or C-terminus of the Chk1 polypeptide.

One useful fusion protein is a GST-Chk1 fusion protein in which the Chk1 sequences are fused to the C-terminus of the GST sequences. Such fusion proteins can facilitate the purification of recombinant Chk1.

Another useful Chk1 fusion protein is an Chk1 -immunoglobulin fusion protein in which all or part of Chk1 is fused to sequences derived from a member of the immunoglobulin protein family. Chk1 -immunoglobulin fusion proteins of the invention can be used as immunogens to produce anti-Chk1 antibodies in a subject, to purify Chk1 ligands and in screening assays to identify molecules which inhibit the interaction of Chk1 with a protein or nucleic acid which binds Chk1.

A Chk1 chimeric or fusion protein can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al. eds., John Wiley & Sons: 1992). Moreover, many expression vectors are commercially available that already encode a fusion moiety (e.g., a GST polypeptide). An Chk1 -encoding nucleic acid can be cloned into such an expression vector such that the fusion moiety is linked in-frame to the Chk1 protein.

Variants of Chk1 protein which function as either Chk1 agonists (mimetics) or as Chk1 antagonists are useful in the methods of the invention. Variants of the Chk1 protein can be generated by mutagenesis, e.g., discrete point mutation or truncation of the Chk1 protein. An agonist of the Chk1 protein can retain substantially the same, or a subset, of the biological activities of the naturally occurring form of the Chk1 protein. An antagonist of the Chk1 protein can inhibit one or more of the activities of the naturally-occurring form of the Chk1 protein by, for example, competitively binding to polynucleotides or proteins involved in Chk1 function. Thus, specific biological effects can be elicited by treatment with a variant of limited function. Treatment of a subject with a variant having a subset of the biological activities of the naturally-occurring form of the protein can have fewer side effects in a subject relative to treatment with the naturally-occurring form of the Chk1 proteins.

Variants of the Chk1 protein which function as either Chk1 agonists (mimetics) or as Chk1 antagonists can be identified by screening combinatorial libraries of mutants, e.g., truncation mutants, of the Chk1 protein for Chk1 protein agonist or antagonist activity. A library of Chk1 variants can be produced by, for example, enzymatically ligating a mixture of synthetic oligonucleotides into gene sequences such that a degenerate set of potential Chk1 sequences is expressible as individual polypeptides, or alternatively, as a set of larger fusion proteins (e.g., for phage display) containing the set of Chk1 sequences therein. There are a variety of methods which can be used to produce libraries of potential Chk1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Chk1 sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the Chk1 protein coding sequence can be used to generate a variegated population of Chk1 fragments for screening and subsequent selection of variants of a Chk1 protein. For example, a library of coding sequence fragments can be generated by treating a double stranded PCR fragment of a Chk1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the Chk1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Chk1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify Chk1 variants (Arkin and Yourvan (1992) Proc. Natl. Acad. Sci. USA 89:7811–7815; Delgrave et al. (1993) Protein Engineering 6(3):327–331).

An isolated Chk1 protein, or a portion or fragment thereof, can be used as an immunogen to generate antibodies that bind Chk1 using standard techniques for polyclonal and monoclonal antibody preparation. The full-length Chk1 protein can be used or, alternatively, the invention provides antigenic peptide fragments of Chk1 for use as immunogens. The antigenic peptide of Chk1 comprises at least 8 (preferably 10, 15, 20, or 30) amino acid residues of the amino acid sequence shown in SEQ ID NO:2 and encompasses an epitope of Chk1 such that an antibody raised against the peptide forms a specific immune complex with Chk1.

Preferred epitopes encompassed by the antigenic peptide are regions of Chk1 that are located on the surface of the protein, e.g., hydrophilic regions.

A Chk1 immunogen typically is used to prepare antibodies by immunizing a suitable subject, (e.g., rabbit, goat, mouse or other mammal) with the immunogen. An appropriate immunogenic preparation can contain, for example, recombinantly expressed Chk1 protein or a chemically synthesized Chk1 polypeptide. The preparation can further include an adjuvant, such as Freund's complete or incomplete adjuvant, or similar immunostimulatory agent. Immunization of a suitable subject with an immunogenic Chk1 preparation induces a polyclonal anti-Chk1 antibody response.

Anti-Chk1 antibodies are useful in the methods of the invention. The term antibody refers to immunoglobulin molecules and immunologically active portions of immunoglobulin molecules, i.e., molecules that contain an antigen binding site which specifically binds an antigen, such as Chk1. A molecule which specifically binds to Chk1 is a molecule which binds Chk1, but does not substantially bind other molecules in a sample, e.g., a biological sample, which naturally contains Chk1. Examples of immunologically active portions of immunoglobulin molecules include F(ab) and F(ab')$_2$ fragments which can be generated by treating the antibody with an enzyme such as pepsin. The term monoclonal antibody or monoclonal antibody composition refers to a population of antibody molecules that contain only one species of an antigen binding site capable of immunoreacting with a particular epitope of Chk1. A monoclonal antibody composition thus typically displays a single binding affinity for a particular Chk1 protein with which-it immunoreacts.

Polyclonal anti-Chk1 antibodies can be prepared as described above by immunizing a suitable subject with a Chk1 immunogen. The anti-Chk1 antibody titer in the immunized subject can be monitored over time by standard techniques, such as with an enzyme linked immunosorbent assay (ELISA) using immobilized Chk1. If desired, the antibody molecules directed against Chk1 can be isolated from the mammal (e.g., from the blood) and further purified by well-known techniques, such as protein A chromatography to obtain the IgG fraction. At an appropriate time after immunization, e.g., when the anti-Chk1 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a Chk1 immunogen as described above, and the culture supernatants of the resulting hybridoma cells are screened to identify a hybridoma producing a monoclonal antibody that binds Chk1.

Any of the many well known protocols used for fusing lymphocytes and immortalized cell lines can be applied for the purpose of generating an anti-Chk1 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New.York, N.Y. (1980); and Lerner (1981) Yale J. Biol. Med., 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Chk1, e.g., using a standard ELISA assay.

Alternative to preparing monoclonal antibody-secreting hybridomas, a monoclonal anti-Chk1 antibody can be identified and isolated by screening a recombinant combinatorial immunoglobulin library (e.g., an antibody phage display library) with Chk1 to thereby isolate immunoglobulin library members that bind Chk1. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J 12:725–734.

Additionally, recombinant anti-Chk1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res.47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-Chk1 antibody (e.g., monoclonal antibody) can be used to isolate Chk1 by standard techniques, such as affinity chromatography or immunoprecipitation. An anti-Chk1 antibody can facilitate the purification of natural Chk1 from cells and of recombinantly produced Chk1 expressed in host cells. Moreover, an anti-Chk1 antibody can be used to detect Chk1 protein (e.g., in a cellular lysate or cell supernatant) in order to evaluate the abundance and pattern of expression of the Chk1 protein. Anti-Chk1 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Vectors, preferably expression vectors, containing a nucleic acid encoding Chk1 (or a portion thereof) are useful in the methods of the invention. A vector is a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors, e.g., viral vectors, replication defective retroviruses, adenoviruses and adeno-associated viruses).

Useful recombinant expression vectors comprise a Chk1 nucleic acid in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. An expression vector can be introduced into host cells to thereby produce proteins or peptides, including fusion proteins or peptides, encoded by nucleic acids as described herein (e.g., Chk1 proteins, mutant forms of Chk1, fusion proteins, etc.).

The recombinant expression vectors of the invention can be designed for expression of Chk1 in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include PGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET lid (Studier et al., Gene Expression Technology: *Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET lid vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident 1 prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, Gene Expression Technology: *Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

An Chk1 expression vector is a yeast expression vector. Examples of vectors for expression in yen be a S. cerivisae include pYepSecl (Baldari et al. (1987) *EMBO J.* 6:229–234), pMFa (Kurjan and Herskowitz, (1982) Cell 30:933–943), pJRY88 (Schultz et al. (1987) *Gene* 54:113–123), pYES2 (Invitrogen Corporation, San Diego, Calif.), and picZ (InVitrogen Corp, San Diego, Calif.).

Alternatively, Chk1 can be expressed in insect cells using baculovirus expression vectors. Baculovirus vectors available for expression of proteins in cultured insect cells (e.g., Sf.9 cells) include the pAc series (Smith et al. (1983) *Mol. Cell Biol.* 3:2156–2165) and the pVL series (Lucklow and Summers (1989) *Virology* 170:31–39).

An Chk1 nucleic acid can be expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natil. Acad. Sci.* USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Also useful in the methods of the invention are recombinant expression vectors comprising an Chk1 nucleic acid molecule cloned into the expression vector in an antisense orientation. That is, the DNA molecule is operatively linked to a regulatory sequence in a manner which allows for expression (by transcription of the DNA molecule) of an RNA molecule which is antisense to Chk1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes See Weintraub et al., Reviews—*Trends in Genetics*, Vol. 1(1) 1986.

Host cells into which an Chk1 expression vector has been introduced are useful in certain metods of the invention. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Chk1 protein can be expressed in bacterial cells such as *E. col*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Chk1 or can be introduced on a separate vector. Cells stably transfected with the introduced nucleic acid can be identified by drug selection (e.g., cells that have incorporated the selectable marker gene will survive, while the other cells die).

A prokaryotic or eukaryotic host cell in culture can be used to produce (i.e., express) Chk1 protein, e.g., by culturing the host cell (into which a recombinant expression vector encoding Chk1 has been introduced) in a suitable medium such that Chk1 protein is produced. Chk1 protein can then be isolated from the medium or the host cell.

Host cells which are capable of expressing Chk1 can also be used to produce nonhuman transgenic animals. For example, in one embodiment, a host cell of the invention is a fertilized oocyte or an embryonic stem cell into which Chk1 -coding sequences have been introduced. Such host cells can then be used to create non-human transgenic animals in which exogenous Chk1 sequences have been introduced into their genome or homologous recombinant animals in which endogenous Chk1 sequences have been altered. Such animals are useful for studying the function and/or activity of Chk1 and for identifying and/or evaluating modulators of Chk1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous Chk1 gene has been altered by homologous recombination between the endogenous gene and an exogenous DNA molecule introduced into a cell of the animal, e.g., an embryonic cell of the animal, prior to development of the animal.

A transgenic animal can be created by introducing Chk1 -encoding nucleic acid into the male pronuclei of a fertilized oocyte, e.g., by microinjection, retroviral infection, and allowing the oocyte to develop in a pseudopregnant female foster animal. The Chk1 cDNA sequence, e.g., that of SEQ ID NO:1 or SEQ ID NO:3 can be introduced as a transgene into the genome of a non-human animal. Alternatively, a nonhuman homologue of the human Chk1 gene, such as a mouse Chk1 gene, can be isolated based on hybridization to the human Chk1 cDNA and used as a transgene. Intronic sequences and polyadenylation signals can also be included in the transgene to increase the efficiency of expression of the transgene. A tissue-specific regulatory sequence(s) can be operably linked to the Chk1 transgene to direct expression of Chk1 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the Chk1 transgene in its genome and/or expression of Chk1 mRNA in tissues or cells of the animals. A transgenic founder animal can then be used to breed additional animals carrying the transgene. Moreover, transgenic animals carrying a transgene encoding Chk1 can further be bred to other transgenic animals carrying other transgenes.

To create an homologous recombinant animal, a vector is prepared which contains at least a portion of a Chk1 gene (e.g., a human or a non-human homolog of the Chk1 gene, e.g., a murine Chk1 gene) into which a deletion, addition or substitution has been introduced to thereby alter, e.g., functionally disrupt, the Chk1 gene. In a preferred embodiment, the vector is designed such that, upon homologous recombination, the endogenous Chk1 gene is functionally disrupted (i.e., no longer encodes a functional protein; also referred to as a "knock out" vector). Alternatively, the vector can be designed such that, upon homologous recombination, the endogenous Chk1 gene is mutated or otherwise altered but still encodes functional protein (e.g., the upstream regulatory region can be altered to thereby alter the expression of the endogenous Chk1 protein). In the homologous recombination vector, the altered portion of the Chk1 gene is flanked at its 5' and 3' ends by additional nucleic acid of the Chk1 gene to allow for homologous recombination to occur between the exogenous Chk1 gene carried by the vector and an endogenous Chk1 gene in an embryonic stem cell. The additional flanking Chk1 nucleic acid is of sufficient length for successful homologous recombination with the endogenous gene. Typically, several kilobases of flanking DNA (both at the 5' and 3' ends) are included in the vector (see e.g., Thomas and Capecchi (1987) *Cell* 51:503 for a description of homologous recombination vectors). The vector is introduced into an embryonic stem cell line (e.g., by electroporation) and cells in which the introduced Chk1 gene has homologously recombined with the endogenous Chk1 gene are selected (see e.g., Li et al. (1992) *Cell* 69:915). The selected cells are then injected into a blastocyst of an animal (e.g., a mouse) to form aggregation chimeras (see, e.g., Bradley in Teratocarcinomas and Embryonic Stem Cells: *A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

Transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of Saccharomyces cerevisiae (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

Chk1 proteins, and anti-Chk1 antibodies, and modulators of Chk1 expression or activity (also referred to herein as "active compounds") can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, NJ) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Chk1 nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci.* USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The Chk1 nucleic acid molecules, proteins, protein homologues, and antibodies described herein can be used in screening assays, predictive medicine (e.g., diagnostic assays, prognostic assays, monitoring clinical trials, and pharmacogenomics), and methods of treatment (e.g., therapeutic treatment methods and prophylactic treatment methods).

A. Screening Assays

The invention provides a method (also referred to herein as a "screening assay") for identifying modulators, i.e., candidate or test compounds or agents (e.g., peptides, peptidomimetics, small molecules or other drugs) which bind to Chk1 proteins or have a stimulatory or inhibitory effect on, for example, Chk1 expression or Chk1 activity. Such identified compounds may be useful for the modulation of drug resistance. In one embodiment, the invention provides assays for screening candidate or test compounds which bind to or modulate the activity of a Chk1 protein or polypeptide or biologically active portion thereof. The test compounds of the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; and Felici (1991) *J. Mol: Biol.* 222:301–310).

In one embodiment, an assay is a cell-based assay in which a cell which expresses a Chk1 protein, or a biologically active portion thereof, is contacted with a test compound and the ability of the test compound to bind to a Chk1 protein determined. The cell, for example, can be a yeast cell or a cell of mammalian origin. Determining the ability of the test compound to bind to the Chk1 protein can be accomplished, for example, by coupling the test compound with a radioisotope or enzymatic label such that binding of the test compound to the Chk1 protein or biologically active portion thereof can be determined by detecting the labeled compound in a complex. For example, test compounds can be labeled with $^{125}I$, $^{35}C$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a Chk1 protein, or a biologically active portion thereof, with a known compound which binds Chk1 to form an assay mixture, contacting the assay mixture with a test compound, and determining the ability of the test compound to interact with a Chk1 protein, wherein determining the ability of the test compound to interact with a Chk1 protein comprises determining the ability of the test compound to preferentially bind to Chk1 or a biologically active portion thereof as compared to the known compound.

In another embodiment, an assay is a cell-based assay comprising contacting a cell expressing a Chk1 protein, or a Biologically active portion thereof, with a test compound and determining the ability of the test compound to modulate (e.g., stimulate or inhibit) the activity of the Chk1 protein or biologically active portion thereof. Determining the ability of the test compound to modulate the activity of Chk1 or a biologically active portion thereof can be accomplished, for example, by determining the ability of the Chk1 protein to bind to or interact with a Chk1 target molecule. As used herein, a "target molecule" is a molecule with which a Chk1 protein binds or interacts in nature, for example, a molecule in the .nucleus or cytoplasm of a cell which expresses a Chk1 protein. A Chk1 target molecule can be a non-Chk1 molecule or a Chk1 protein or polypeptide. The target, for example, can be a second intracellular protein which has catalytic activity, a protein which naturally binds to Chk1, or a protein which facilitates the association of DNA with Chk1.

Determining the ability of the Chk1 protein to bind to or interact with a Chk1 target molecule can be accomplished by one of the methods described above for determining direct binding. In a preferred embodiment, determining the ability of the Chk1 protein to bind to or interact with a Chk1 target molecule can be accomplished by determining the activity of the target molecule or detecting a cellular response, for example, cell survival or cell proliferation in the presence of a chemotherapeutic drug.

In yet another embodiment, an assay of the present invention is a cell-free assay comprising contacting a Chk1 protein or biologically active portion thereof with a test compound and determining the ability of the test compound to bind to the Chk1 protein or biologically active portion thereof. Binding of the test compound to the Chk1 protein can be determined either directly or indirectly as described above. In a preferred embodiment, the assay includes contacting the Chk1 protein or biologically active portion thereof with a known compound which binds Chk1 to form an assay mixture, contacting the assay mixture with a test compound, and determining the ability of the test compound to interact with a Chk1 protein, wherein determining the ability of the test compound to interact with a Chk1 protein comprises determining the ability of the test compound to Zpreferentially bind to Chk1 or biologically active portion thereof as compared to the known compound.

In another embodiment, an assay is a cell-free assay comprising contacting Chk1 protein or biologically active portion thereof with a test compound and determining the ability of the test compound to modulate (e.g., stimulate or inhibit) the activity of the Chk1 protein or biologically active portion thereof. Determining the ability of the test compound to modulate the activity of Chk1 can be accomplished, for example, by determining the ability of the Chk1 protein to bind to a Chk1 target molecule by one of the methods described above for determining direct binding. In an alternative embodiment, determining the ability of the test compound to modulate the activity of Chk1 can be accomplished by determining the ability of the Chk1 protein further modulate a Chk1 target molecule. For example, the catalytic/enzymatic activity of the target molecule on an appropriate substrate can be determined as previously described.

In yet another embodiment, the cell-free assay comprises contacting the Chk1 protein or biologically active portion thereof with a known compound which binds Chk1 to form an assay mixture, contacting the assay mixture with a test compound, and determining the ability of the test compound to interact with a Chk1 protein, wherein determining the ability of the test compound to interact with a Chk1 protein comprises determining the ability of the Chk1 protein to preferentially bind to or modulate the activity of a Chk1 target molecule.

The cell-free assays of the present invention are amenable to use of both native and variant forms (e.g., peptide fragments and fusion proteins) of Chk1. In the case of cell-free assays comprising a hydrophobic form of Chk1, it may be desirable to utilize a solubilizing agent such that the hydrophobic form of Chk1 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either Chk1 or its target molecule to facilitate separation of complexed from uncomplexed forms of one or both of the proteins, as well as to accommodate automation of the assay. Binding of a test compound to Chk1, or interaction of Chk1 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/Chk1 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or Chk1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of Chk1 binding or activity determined using standard techniques.

Other techniques for immobilizing proteins on matrices can also be used in the screening assays of the invention. For example, either Chk1 or its target molecule can be immobilized utilizing conjugation of biotin and streptavidin. Biotinylated Chk1 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with Chk1 or target molecules but which do not interfere with binding of the Chk1 protein to its target molecule can be derivatized to the wells of the plate, and unbound target or Chk1 trapped in the wells by antibody conjugation. Methods for detecting such complexes, in addition to those described above for the GST-immobilized complexes, include immunodetection of complexes using antibodies reactive with the Chk1 or target molecule, as well as enzyme-linked assays which rely on detecting an enzymatic activity associated with the Chk1 or target molecule.

In another embodiment, modulators of Chk1 expression are identified in a method in which a cell is contacted with a candidate compound and the expression of Chk1 (mRNA or protein, or the copy number of the Chk1 gene) in the cell is determined. The level of expression of Chk1 in the presence of the candidate compound is compared to the level of expression of Chk1 in the absence of the candidate compound. The candidate compound can then be identified as a modulator of Chk1 expression based on this comparison. For example, when expression of Chk1 mRNA or protein is greater (statistically significantly greater) in the presence of the candidate compound than in its absence, the candidate compound is identified as a stimulator of Chk1 mRNA or protein expression. Alternatively, when expression of Chk1 mRNA or protein is less (statistically significantly less) in the presence of the candidate compound than in its absence, the candidate compound is identified as an inhibitor of Chk1 mRNA or protein expression. The level of Chk1 mRNA or protein expression in the cells, or the number of Chk1 gene copies per cell can be determined by methods described herein for detecting Chk1 genomic DNA, mRNA, or protein.

Chk1 proteins can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Dio/Techniques* 14:920–924; Iwabuchi et al. (1993) *Oncogene* 8:1693–1696; and WO94/10300), to identify other proteins, which bind to or interact with Chk1 ("Chk1-binding proteins" or "Chk1-bp") and modulate Chk1 activity.

The two-hybrid system is based on the modular nature of most transcription factors, which consist of separable DNA-binding and activation domains. Briefly, the assay utilizes two different DNA constructs. In one construct, the gene that codes for Chk1 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an Chk1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with Chk1.

This invention further pertains to novel agents identified by the above-described screening assays and uses thereof for treatments as described herein.

B. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining Chk1 protein and/or nucleic acid expression as well as Chk1 activity, in the context of a biological sample (e.g., blood, serum, cells, tissue) to thereby determine whether an individual is afflicted with a disease or disorder, or is at risk of developing a disorder, associated with aberrant Chk1 expression or activity (e.g., altered drug resistance). The invention also provides for prognostic (or predictive) assays for determining whether an individual is at risk of developing a disorder associated with Chk1 protein, nucleic acid expression or activity (e.g., altered drug resistance). For example, mutations in a Chk1 gene can be assayed in a biological sample. Such assays can be used for prognostic or predictive purpose to thereby prophylactically treat an individual prior to the onset of a disorder characterized by or associated with Chk1 protein, nucleic acid expression or activity. For example, because Chk1 is expressed at a higher level in drug resistant cells (e.g., the doxorubicin resistant cell lines A2780, U937, and HL60) than non-drug resistant cell lines, higher than normal expression of Chk1 can be used as an indicator of drug resistance.

Another aspect of the invention provides methods for determining Chk1 protein, nucleic acid expression or Chk1 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of Chk1 in clinical trials.

These and other agents are described in further detail in the following sections.

1. Diagnostic Assays

The invention provides a method of assessing expression, especially undesirable expression, of a cellular Chk1 gene. Undesirable (e.g., excessive) expression may indicate the presence, persistence or reappearance of drug-resistant (e.g., vinblastin-resistant) tumor cells in an individual's tissue. More generally, aberrant expression may indicate the occurrence of a deleterious or disease-associated phenotype contributed to by Chk1.

An exemplary method for detecting the presence or absence of Chk1 in a biological sample involves obtaining a biological sample (preferably from a body site implicated in a possible diagnosis of diseased or malignant tissue) from a test subject and contacting the biological sample with a compound or an agent capable of detecting Chk1 protein or nucleic acid (e.g., mRNA, genomic DNA) that encodes Chk1 protein such that the presence of Chk1 is detected in the biological sample. The presence and/or relative abundance of Chk1 indicates aberrant or undesirable expression of a cellular Chk1 gene, and correlates with the occurrence in situ of cells having a drug-resistant phenotype.

A preferred agent for detecting Chk1 mRNA or genomic DNA is a labeled nucleic acid probe capable of hybridizing to Chk1 mRNA or genomic DNA. The nucleic acid probe can be, for example, a full-length Chk1 nucleic acid, such as the nucleic acid of SEQ ID NO: 1 or 3, or a portion thereof, such as an oligonucleotide of at least 15, 30, 50, 100, 250 or 500 nucleotides in length and sufficient to specifically hybridize under stringent conditions to Chk1 mRNA or genomic DNA. Other suitable probes for use in the diagnostic assays of the invention are described herein.

A preferred agent for detecting Chk1 protein is an antibody capable of binding to Chk1 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Chk1 mRNA, protein, or genomic DNA in a biological sample in vitro as well as in vivo. For example, in vitro techniques for detection of Chk1 mRNA include Northern hybridizations and in situ hybridizations. In vitro techniques for detection of Chk1 protein include enzyme linked immunosorbent assays (ELISAs), Western blots, immunoprecipitations and immunofluorescence. In vitro techniques for detection of Chk1 genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting Chk1 protein, mRNA, or genomic DNA, such that the presence of Chk1 protein, mRNA or genomic DNA is detected in the biological sample, and comparing the presence of Chk1 protein, mRNA or genomic DNA in the control sample with the presence of Chk1 protein, mRNA or genomic DNA in the test sample.

The invention also encompasses kits for detecting the presence of Chk1 in a biological sample (a test sample). Such kits can be used to determine if a subject is suffering from or is at increased risk of developing a disorder associated with aberrant expression of Chk1 (e.g., the presence of a drug resistance cancer). For example, the kit can comprise a labeled compound or agent capable of detecting Chk1 protein or mRNA in a biological sample and means for determining the amount of Chk1 in the sample (e.g., an anti-Chk1 antibody or an oligonucleotide probe which binds to DNA encoding Chk1, e.g., SEQ ID NO:1 or SEQ ID NO:3). Kits may also include instruction for observing that the tested subject is suffering from or is at risk of developing a disorder associated with aberrant expression of Chk1 if the amount of Chk1 protein or mRNA is above or below a normal level.

For antibody-based kits, the kit may comprise, for example: (1) a first antibody (e.g., attached to a solid support) which binds to Chk1 protein; and, optionally, (2) a second, different antibody which binds to Chk1 protein or the first antibody and is conjugated to a detectable agent.

For oligonucleotide-based kits, the kit may comprise, for example: (1) a oligonucleotide, e.g., a detectably labelled oligonucleotide, which hybridizes to a Chk1 nucleic acid sequence or (2) a pair of primers useful for amplifying a Chk1 nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of Chk1.

2. Prognostic Assays

The methods described herein can furthermore be utilized as diagnostic or prognostic assays to identify subjects having or at risk of developing a disease or disorder associated with aberrant Chk1 expression or activity. For example, the assays described herein, such as the preceding diagnostic assays or the following assays, can be utilized to identify a subject having or at risk of developing a disorder associated with aberrant Chk1 protein, nucleic acid expression or activity (eg., the presence of drug resistant tumor cells). Alternatively, the prognostic assays can be utilized to identify a subject having or at risk for developing such a disease or disorder. Thus, the present invention provides a method in which a test sample is obtained from a subject and Chk1 protein or nucleic acid (e.g., mRNA, genomic DNA) is detected, wherein the presence or relative quantity of Chk1 protein or nucleic acid is diagnostic for a subject having or at risk of developing a disease or disorder associated with aberrant Chk1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Chk1 expression or activity. Thus, if increased Chk1 expression is a cause of increased drug resistance, such methods can be used to determine whether a subject can be effectively treated with a specific agent or class of agents (e.g., agents of a type which decrease Chk1 activity). Thus, the present invention provides methods for determining whether a subject can be effectively treated with an agent for a disorder associated with aberrant Chk1 expression or activity in which a test sample is obtained and Chk1 protein or nucleic acid is detected (e.g., wherein the presence or relative quantity of Chk1 protein or nucleic acid is diagnostic for a subject that can be administered the agent to treat a disorder associated with aberrant Chk1 expression or activity). In some embodiments, the foregoing methods provide information useful in prognostication, staging and management of malignancies (tumors) that are characterized by altered expression of Chk1 and thus by a drug-resistance phenotype. The information more specifically assists the clinician in designing chemotherapeutic or other treatment regimes to eradicate such malignancies from the body of an afflicted subject.

The methods of the invention can also be used to detect genetic lesions (e.g., mutations or amplifications) in a Chk1 gene, thereby determining if a subject with the altered gene is at risk for a disorder characterized by aberrant cell proliferation and/or differentiation. For example, genetic mutations, whether of germline or somatic origin, may indicate whether the process of developing drug resistance has been initiated or is likely to arise in the tested cells. In preferred embodiments, the methods include detecting, in a sample of cells from the subject, the presence or absence of a genetic lesion characterized by at least one of an alteration affecting the integrity of a gene encoding a Chk1-protein, the mis-expression of the Chk1 gene, or the amplification of a Chk1 gene. Preferably the sample of cells is obtained from a body tissue suspected of comprising transformed cells (e.g., cancer cells). Thus, the present method provides information relevant to diagnosis of the presence of a tumor.

Genetic lesions can be detected, for example, by ascertaining the existence of at least one of 1) a deletion of one or more nucleotides from a Chk1 gene; 2) an addition of one or more nucleotides to a Chk1 gene; 3) a substitution of one or more nucleotides of a Chk1 gene, 4) a chromosomal rearrangement of a Chk1 gene; 5) an alteration in the level of a messenger RNA transcript of a Chk1 gene, 6) aberrant modification of a Chk1 gene, such as of the methylation pattern of the genomic DNA, 7) the presence of a non-wild type splicing pattern of a messenger RNA transcript of a Chk1 gene, 8) a non-wild type level of a Chk1-protein, 9) allelic loss of a Chk1 gene, 10) amplification of a Chk1 gene, and 11) inappropriate post-translational modification of a Chk1-protein. As described herein, there are a large number of assay techniques known in the art which can be used for detecting lesions in a Chk1 gene. A preferred biological sample is a biopsy sample of tissue suspected of comprising transformed cells isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the Chk1 gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a Chk1 gene under conditions such that hybridization and amplification of the Chk1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli et al. (1990) *Proc. Nati. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Chk1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in Chk1 can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in Chk1 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Chk1 gene and detect mutations by comparing the sequence of the sample Chk1 with the corresponding wild-type (control) sequence. Additionally, sequencing of the DNA flanking the Chk1 can be used to determine if the Chk1 gene has been amplified. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the Chk1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type Chk1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Chk1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Chk1 sequence, e.g., a wild-type Chk1 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in Chk1 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet Anal Tech Appl* 9:73–79). Single-stranded DNA fragments of sample and control Chk1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Chk1 gene.

Furthermore, any cell type or tissue, preferably biopsy samples of tissue comprising or suspected of comprising transformed cells, in which Chk1 is expressed may be utilized in the prognostic assays described herein.

3. Pharmacogenomics

Agents, or modulators which have a stimulatory or inhibitory effect on Chk1 activity (e.g., Chk1 gene expression) as identified by a screening assay described herein can be administered to individuals to treat (prophylactically or therapeutically) disorders (e.g., drug-resistance) associated with aberrant Chk1 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of Chk1 protein, expression of Chk1 nucleic acid, or mutation content of Chk1 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2): 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of Chk1 protein, expression of Chk1 nucleic acid, or mutation content of Chk1 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a Chk1 modulator, such as a modulator identified by one of the exemplary screening assays described herein.

4. Monitoring of Effects During Clinical Trials

Monitoring the influence of agents (e.g., drugs, compounds) on the expression or activity of Chk1 (e.g., the ability to modulate the drug-resistant phenotype of a cell) can be applied not only in basic drug screening, but also in clinical trials. For example, the effectiveness of an agent determined by a screening assay as described herein to decrease Chk1 gene expression, protein levels, or down-regulate Chk1 activity, can be monitored in clinical trails of subjects exhibiting increased Chk1 gene expression, protein levels, or upregulated Chk1 activity.

Alternatively, the effectiveness of an agent determined by a screening assay to increase Chk1 gene expression, protein levels, or upregulate Chk1 activity (e.g., to increase the drug resistance of a non-cancerous cell), can be monitored in clinical trials of compounds designed to increase Chk1 gene expression, protein levels, or upregulate Chk1 activity. In such clinical trials, the expression or activity of Chk1 and, preferably, other genes that have been implicated in, for example, a cellular proliferation disorder, can be used as a "read out" or markers of the drug resistance of a particular cell.

For example, and not by way of limitation, genes, including Chk1, that are modulated in cells by treatment with an agent (e.g., compound, drug or small molecule) which modulates Chk1 activity (e.g., identified in a screening assay as described herein) can be identified. Thus, to study the effect of agents on cellular proliferation disorders, for example, in a clinical trial, cells can be isolated and RNA prepared and analyzed for the levels of expression of Chk1 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Chk1 or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Chk1 protein, mRNA, or genomic DNA in the preadministration sample; (iii) obtaining one or more post-administration samples from the subject; (iv) detecting the level of expression or activity of the Chk1 protein, mRNA, or genomic DNA in the post-administration samples; (v) comparing the level of expression or activity of the Chk1 protein, mRNA, or genomic DNA in the pre-administration sample with the Chk1 protein, mRNA, or genomic DNA in the post administration sample or samples; and (vi) altering the administration of the agent to the subject accordingly. For example, increased administration of the agent may be desirable to decrease the expression or activity of Chk1 to higher levels than detected, i.e., to increase the effectiveness of the agent.

C. Methods of Treatment

The present invention provides for both prophylactic and therapeutic methods of treating a subject at risk of (or susceptible to) a disorder or having a disorder associated with aberrant Chk1 expression or activity. Such disorders include cellular resistance to chemotherapeutic drugs.

1. Prophylactic Methods

In one aspect, the invention provides a method for preventing in a subject, a disease or condition associated with an aberrant Chk1 expression or activity (e.g., the development of drug resistance), by administering to the subject an agent which modulates Chk1 expression or at least one Chk1 activity. Subjects at risk for a condition which is caused or contributed to by aberrant Chk1 expression or activity can be identified by, for example, any or a combination of diagnostic or prognostic assays as described herein. Administration of a prophylactic agent can occur prior to the manifestation of symptoms characteristic of the Chk1 aberrancy, such that a disease or disorder is prevented or, alternatively, delayed in its progression. For example, administration of a prophylatic agent to a cancer patient may prevent or delay the development of drug resistance in the patient's cancer cells. Depending on the type of Chk1 aberrancy, for example, a Chk1 agonist or Chk1 antagonist agent can be used for treating the subject. The appropriate agent can be determined based on screening assays described herein.

2. Therapeutic Methods

Another aspect of the invention pertains to methods of modulating Chk1 expression or activity for therapeutic purposes. For example, the effectiveness of chemotherapy is "potentiated" (enhanced) by restoring or improving vulnerability of the transformed cells to the cytotoxic effects of a chemotherapeutic drug that otherwise would be less effective by reducing the expression of Chk1 in the cells. The modulatory method of the invention involves contacting a cell with an agent that modulates one or more of the activities of Chk1 protein activity associated with the cell. An agent that modulates Chk1 protein activity can be an agent as described herein, such as a nucleic acid or a protein, a naturally-occurring cognate ligand of a Chk1 protein, a peptide, a Chk1 peptidomimetic, or other small molecule. In one embodiment, the agent stimulates one or more of the biological activities of Chk1 protein. Examples of such stimulatory agents include active Chk1 protein and a nucleic acid molecule encoding Chk1 that has been introduced into the cell. In another embodiment, the agent inhibits one or more of the biological activities of Chk1 protein. Examples of such inhibitory agents include antisense Chk1 nucleic acid molecules and anti-Chk1 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a Chk1 protein or nucleic acid molecule. In one embodiment, the method involves administering an agent (e.g., an agent identified by a screening assay described herein), or combination of agents that modulates (e.g., upregulates or downregulates) Chk1 expression or activity. In another embodiment, the method involves administering a Chk1 protein or nucleic acid molecule as therapy to compensate for reduced or aberrant Chk1 expression or activity.

For example, in one embodiment, the method involves administering the desired drug (e.g., cyclophosphamide) to an individual afflicted with a drug-resistant cell population (a tumor, e.g., a carcinoma, sarcoma, leukemia, lymphoma, or lymphosarcoma), and coadministering an inhibitor of Chk1 expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an Chk1 antisense oligonucleotide in combination with one or more other antisense oligonucleotides) can be administered to the individual sufficiently in advance of administration of the chemotherapeutic drug to allow the antisense composition to permeate the individual's tissues, especially tissue comprising the transformed cells to be eradicated; to be internalized by transformed cells; and to disrupt Chk1 gene expression and/or protein production.

Iinhibition of Chk1 activity is desirable in situations in which Chk1 is abnormally upregulated and/or in which decreased Chk1 activity is likely to have a beneficial effect, e.g., in decreasing the drug resistance of a cancer cell. Conversely, stimulation of Chk1 activity is desirable in situations in which Chk1 is abnormally downregulated and/ or in which increased Chk1 activity is likely to have a beneficial effect, e,g., in increasing the drug resistance of a non-cancer cell.

This invention is further illustrated by the following examples which should not be construed as limiting. The contents of all references, patents and published patent applications cited throughout this application are hereby incorporated by reference.

Example 1

Expression of Chk1 in Normal Cells and Cancer Cells

Northern blot analysis was used to examine the expression of Chk1 in various normal and cancerous tissues. This analysis revealed that Chk1 is expressed at a considerably higher level in breast carcinoma (epithelial cells) than normal breast tissue. The analysis also showed that Chk1 is expressed at a high level in colon carcinoma (epithelial cells). In normal lung, Chk1 is expressed at a lower level than in lung carcinoma, where it is expressed at a high level in epithelial cells. The Northern analysis also showed that Chk1 is expressed at a higher level in prostate carcinoma (ductal epithelial cells) than in normal prostate.

Example 2

Expression of Chk1 in Drug Resistant Cells Lines

A Northertion library was used to analyze differential expression of genes in UCLA cells (American Type Culture Collection Accession No. CRL-1593.2; American Type Culture Collection, 10801 University Boulevard, Manassas, Va. 20110-2209) and resistant variants of UCLA cells. This analysis revealed that Chk1 is expressed at a higher level in the vinblastine resistan t UCLA cells than in the corresponding relatively vinblastine sensitive cells from which the resistant cells were derived. Chk1 i also proved to be upregulated in a variety of relatively adromycin resistant cells lines compared to the relatively adromycin sensitive cells from which the cell lines were derived.

Example 3

Preparation of Chk1 Proteins

Recombinant Chk1 can be produced in a variety of expression systems. For example, the mature Chk1 peptide can be expressed as a recombinant glutathione-S-transferase (GST) fusion protein in insect cells and the fusion protein can be isolated and characterized. For example, a gene encoding a GST-Chk1 fusion protein can be created in the pGEX-2T vector (Promega). The GST-Chk1 fusion gene can be removed from this vector and inserted into the pFastBacl expression vector (Life Technologies, Inc., Bethesda, Md.). This vector permits expression of the fusion protein in cultured insect cells (e.g., Sf9 cells). The cells expressing the fusion protein are lysed and the fusion protein is isolated using a Glutathione Sepharose 4B column (Pharmacia, Inc. Piscataway, N.J.). After elution of the fusion protein from the column, thrombin is used to cleave the GST polypeptide which is then removed using a Glutathione Sepharose 4B column.

The Chk1 protein prepared as described above can be used to generate antibodies directed against Chk1 and in in vitro screening assays used to identify inhibitors of Chk1 activity.

Analysis of purified Chk1 prepared as described above revealed that Chk1 is likely phosphorylated at one or more of the following amino acid residues: $Ser^{360}$, $Ser^{376}$, $Ser^{406}$, and $Thr^{403}$.

Example 4

Reduction in Chk1 Expression Using a Ribozyme

The following experiment indicates that 293 EBNA cells transfected with a vector that expresses a hammerhead ribozyme designed to selectively cleave Chk1 mRNA and thus reduce Chk1 expression are more sensitive to doxorubicin than control cells that are not transfected with the ribozyme expression construct or are transfected with a vector that expresses a mutant ribozyme.

In general, hammerhead ribozymes have the structure shown in FIG. 3. The 5' to 3' strand is the RNA being cleaved, and the 3' to 5' strand is the ribozyme. The arrow indicates the location of the cleavage.

Figure 4A:
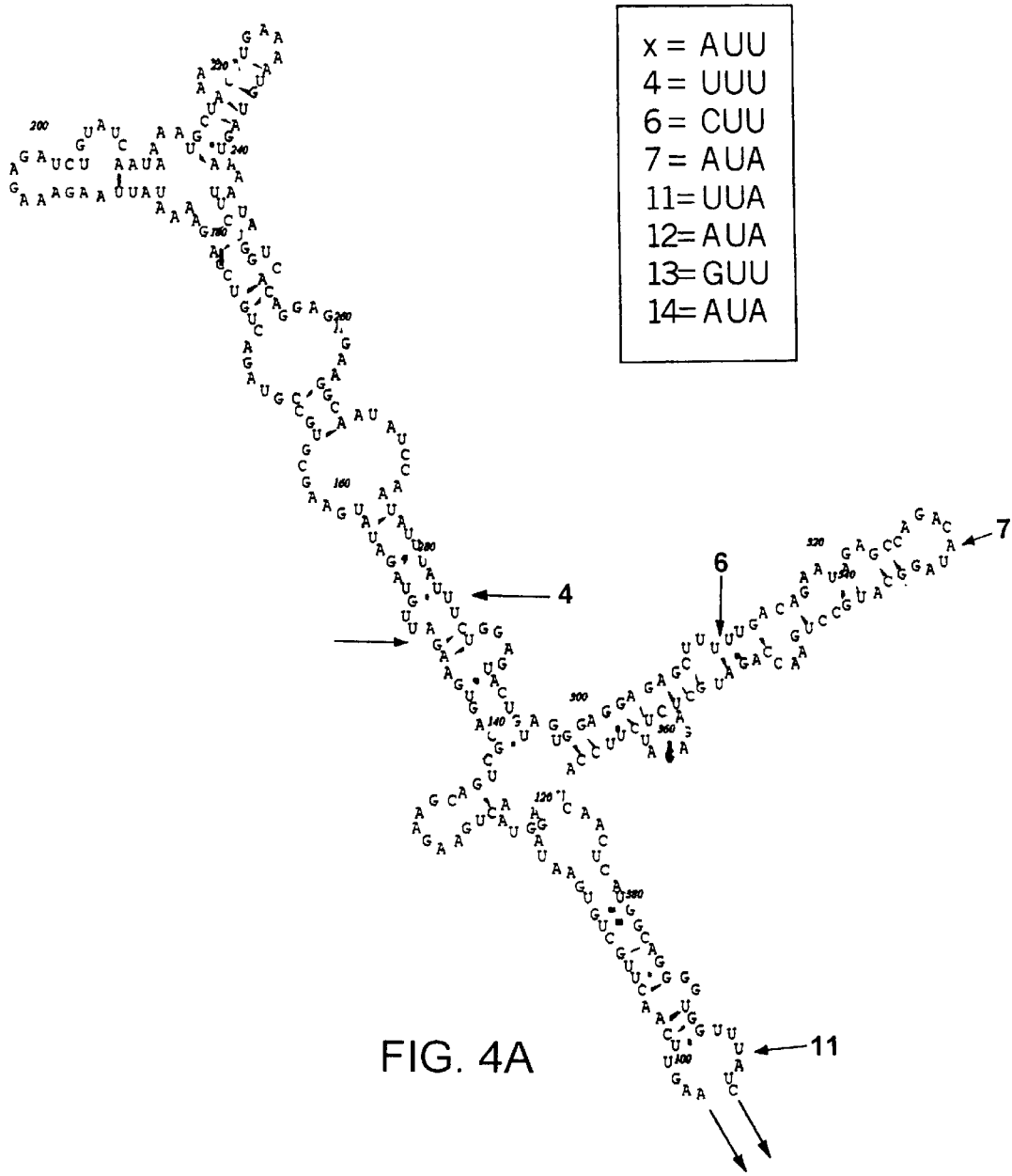
FIGS. 4A and B depicts a predicted secondary structure for Chk1 mRNA.
Figure 4B:
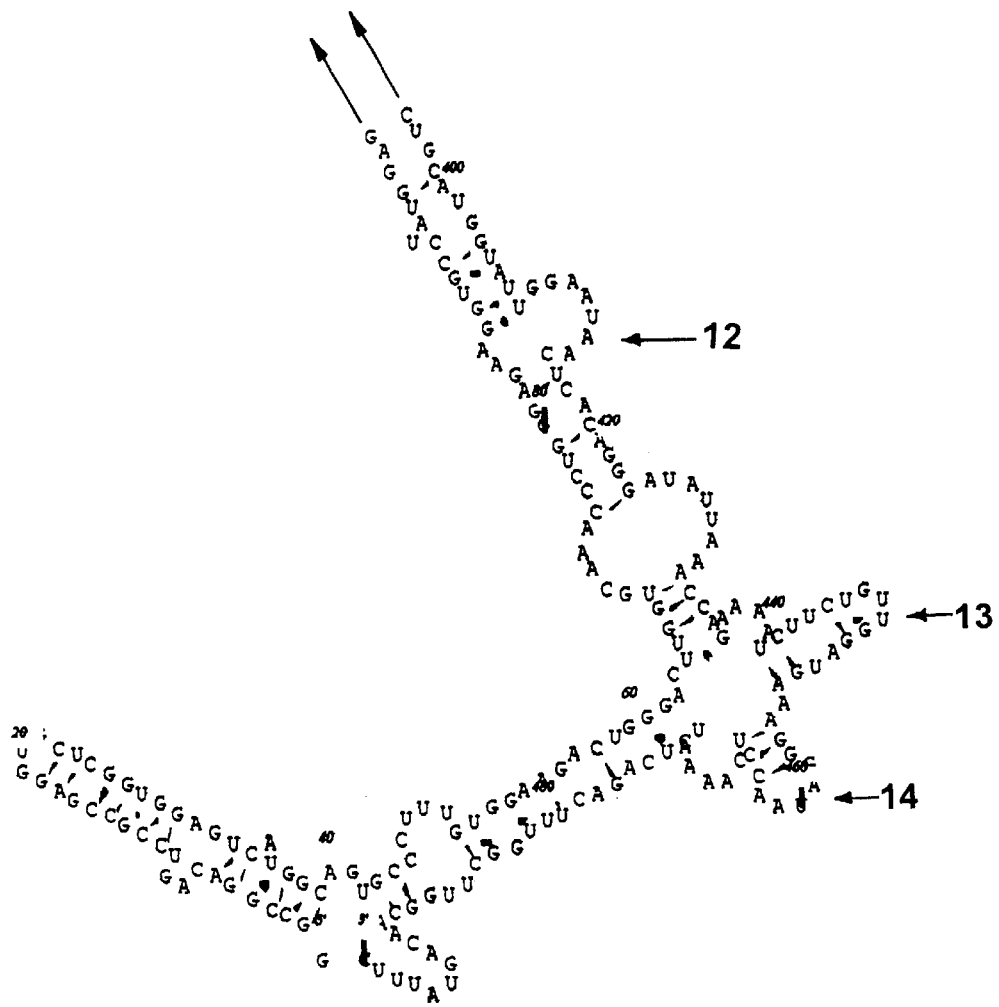

Analysis of the predicted secondary structure of Chk1 mRNA revealed several unpaired regions which might be cleaved by a suitably designed hammerhead ribozyme. Several of these regions were tested for accessibility using an RNaseH assay. Briefly, DNA primers designed to basepair with various predicted unpaired regions were incubated with in vitro transcribed, detectably labeled Chk1 mRNA. The mRNA/primer mixture was exposed to RNAseH, which cleaves the RNA strand of basepaired DNA/RNA hybrids. FIG. 4 depicts a predicted secondary structure of Chk1 mRNA with eight potentially unpaired regions (2, 4, 6, 7, 11, 12, 13, and 14) indicated. These regions include the one or more potential cleavage sites (2: position 234; 4: position 282; 6: positions 309, 311, and 312; 7: position 333; 11: position 392; 12: position 411; 13: positions 441 and 446; 14: positions 460 and 465). The RNAseH analysis suggested that at least region 11 is unpaired. A triple ribozyme designed to cleave this unpaired region was constructed and inserted into and expression vector. A triple ribozyme is a ribozyme which self-processes to release the ribozyme of interest. An expression vector carrying the triple ribozyme construct ("Rz11") designed to cleave within region 11 at position 392 was used to transiently transfect 293EBNA cells. As a control, 293EBNA cells were also transfected with either an expression vector lacking the triple ribozyme construct ("empty") or a an expression vector carrying a mutant, inactive triple ribozyme construct ("Rz11M"). At 24 hr post-transfection the medium was changed. At 48 hr post-transfection the cultures were split and doxorubicin was added to at concentrations up tp 2 micrograms/ml. Cytotoxicity measurements were made at 72, 96, and 120 hr post-transfection (corresponding to 24 hr, 48 hr, and 72 hr of drug treatment). The transfected cells were then grown in the presence of various concentrations of doxorubicin. As shown in FIG. 5, cells transfected with the active triple ribozyme (Rz11) were more sensitive to doxorubicin than the control cells (Rz11M and empty) after 24 hr drug treatment. This result suggests that decreasing the expression of Chk1 can lead to increased drug sensitivity.

Equivalents

---

SEQUENCE LISTING

<160> NUMBER OF SEQ ID NOS: 5

<210> SEQ ID NO 1
<211> LENGTH: 1821
<212> TYPE: DNA
<213> ORGANISM: Homo sapiens
<220> FEATURE:
<221> NAME/KEY: CDS
<222> LOCATION: (35)...(1462)

<400> SEQUENCE: 1

```
ggccggacag tccgccgagg tgctcggtgg agtc atg gca gtg ccc ttt gtg gaa         55
                                    Met Ala Val Pro Phe Val Glu
                                      1               5 gac tgg gac ttg gtg caa acc ctg gga gaa ggt gcc tat gga gaa gtt        103
Asp Trp Asp Leu Val Gln Thr Leu Gly Glu Gly Ala Tyr Gly Glu Val
         10                  15                  20 caa ctt gct gtg aat aga gta act gaa gaa gca gtc gca gtg aag att        151
Gln Leu Ala Val Asn Arg Val Thr Glu Glu Ala Val Ala Val Lys Ile
     25                  30                  35 gta gat atg aag cgt gcc gta gac tgt cca gaa aat att aag aaa gag        199
Val Asp Met Lys Arg Ala Val Asp Cys Pro Glu Asn Ile Lys Lys Glu
 40                  45                  50                  55 atc tgt atc aat aaa atg cta aat cat gaa aat gta gta aaa ttc tat        247
Ile Cys Ile Asn Lys Met Leu Asn His Glu Asn Val Val Lys Phe Tyr
                 60                  65                  70 ggt cac agg aga gaa ggc aat atc caa tat tta ttt ctg gag tac tgt        295
Gly His Arg Arg Glu Gly Asn Ile Gln Tyr Leu Phe Leu Glu Tyr Cys
             75                  80                  85 agt gga gga gag ctt ttt gac aga ata gag cca gac ata ggc atg cct        343
Ser Gly Gly Glu Leu Phe Asp Arg Ile Glu Pro Asp Ile Gly Met Pro
         90                  95                 100 gaa cca gat gct cag aga ttc ttc cat caa ctc atg gca ggg gtg gtt        391
Glu Pro Asp Ala Gln Arg Phe Phe His Gln Leu Met Ala Gly Val Val
    105                 110                 115 tat ctg cat ggt att gga ata act cac agg gat att aaa cca gaa aat        439
Tyr Leu His Gly Ile Gly Ile Thr His Arg Asp Ile Lys Pro Glu Asn
120                 125                 130                 135
```

```
ctt ctg ttg gat gaa agg gat aac ctc aaa atc tca gac ttt ggc ttg       487
Leu Leu Leu Asp Glu Arg Asp Asn Leu Lys Ile Ser Asp Phe Gly Leu
            140                 145                 150 gca aca gta ttt cgg tat aat aat cgt gag cgt ttg ttg aac aag atg       535
Ala Thr Val Phe Arg Tyr Asn Asn Arg Glu Arg Leu Leu Asn Lys Met
        155                 160                 165 tgt ggt act tta cca tat gtt gct cca gaa ctt ctg aag aga aga gaa       583
Cys Gly Thr Leu Pro Tyr Val Ala Pro Glu Leu Leu Lys Arg Arg Glu
    170                 175                 180 ttt cat gca gaa cca gtt gat gtt tgg tcc tgt gga ata gta ctt act       631
Phe His Ala Glu Pro Val Asp Val Trp Ser Cys Gly Ile Val Leu Thr
185                 190                 195 gca atg ctc gct gga gaa ttg cca tgg gac caa ccc agt gac agc tgt       679
Ala Met Leu Ala Gly Glu Leu Pro Trp Asp Gln Pro Ser Asp Ser Cys
200                 205                 210                 215 cag gag tat tct gac tgg aaa gaa aaa aaa aca tac ctc aac cct tgg       727
Gln Glu Tyr Ser Asp Trp Lys Glu Lys Lys Thr Tyr Leu Asn Pro Trp
            220                 225                 230 aaa aaa atc gat tct gct cct cta gct ctg ctg cat aaa atc tta gtt       775
Lys Lys Ile Asp Ser Ala Pro Leu Ala Leu Leu His Lys Ile Leu Val
        235                 240                 245 gag aat cca tca gca aga att acc att cca gac atc aaa aaa gat aga       823
Glu Asn Pro Ser Ala Arg Ile Thr Ile Pro Asp Ile Lys Lys Asp Arg
    250                 255                 260 tgg tac aac aaa ccc ctc aag aaa ggg gca aaa agg ccc cga gtc act       871
Trp Tyr Asn Lys Pro Leu Lys Lys Gly Ala Lys Arg Pro Arg Val Thr
265                 270                 275 tca ggt ggt gtg tca gag tct ccc agt gga ttt tct aag cac att caa       919
Ser Gly Gly Val Ser Glu Ser Pro Ser Gly Phe Ser Lys His Ile Gln
280                 285                 290                 295 tcc aat ttg gac ttc tct cca gta aac agt gct tct agt gaa gaa aat       967
Ser Asn Leu Asp Phe Ser Pro Val Asn Ser Ala Ser Ser Glu Glu Asn
            300                 305                 310 gtg aag tac tcc agt tct cag cca gaa ccc cgc aca ggt ctt tcc tta      1015
Val Lys Tyr Ser Ser Ser Gln Pro Glu Pro Arg Thr Gly Leu Ser Leu
        315                 320                 325 tgg gat acc agc ccc tca tac att gat aaa ttg gta caa ggg atc agc      1063
Trp Asp Thr Ser Pro Ser Tyr Ile Asp Lys Leu Val Gln Gly Ile Ser
    330                 335                 340 ttt tcc cag ccc aca tgt cct gat cat atg ctt ttg aat agt cag tta      1111
Phe Ser Gln Pro Thr Cys Pro Asp His Met Leu Leu Asn Ser Gln Leu
345                 350                 355 ctt ggc acc cca gga tcc tca cag aac ccc tgg cag cgg ttg gtc aaa      1159
Leu Gly Thr Pro Gly Ser Ser Gln Asn Pro Trp Gln Arg Leu Val Lys
360                 365                 370                 375 aga atg aca cga ttc ttt acc aaa ttg gat gca gac aaa tct tat caa      1207
Arg Met Thr Arg Phe Phe Thr Lys Leu Asp Ala Asp Lys Ser Tyr Gln
            380                 385                 390 tgc ctg aaa gag act tgt gag aag ttg ggc tat caa tgg aag aaa agt      1255
Cys Leu Lys Glu Thr Cys Glu Lys Leu Gly Tyr Gln Trp Lys Lys Ser
        395                 400                 405 tgt atg aat cag gtt act ata tca aca act gat agg aga aac aat aaa      1303
Cys Met Asn Gln Val Thr Ile Ser Thr Thr Asp Arg Arg Asn Asn Lys
    410                 415                 420 ctc att ttc aaa gtg aat ttg tta gaa atg gat gat aaa ata ttg gtt      1351
Leu Ile Phe Lys Val Asn Leu Leu Glu Met Asp Asp Lys Ile Leu Val
425                 430                 435 gac ttc cgg ctt tct aag ggt gat gga ttg gag ttc aag aga cac ttc      1399
Asp Phe Arg Leu Ser Lys Gly Asp Gly Leu Glu Phe Lys Arg His Phe
440                 445                 450                 455
```

-continued

```
ctg aag att aaa ggg aag ctg att gat att gtg agc agc cag aag gtt    1447
Leu Lys Ile Lys Gly Lys Leu Ile Asp Ile Val Ser Ser Gln Lys Val
            460                 465                 470 tgg ctt cct gcc aca tgatcggacc atcggctctg gggaatcctg gtgaatatag    1502
Trp Leu Pro Ala Thr
            475 tgctgctatg ttgacattat tcttcctaga gaagattatc ctgtcctgca aactgcaaat    1562 agtagttcct gaagtgttca cttccctgtt tatccaaaca tcttccaatt tattttgttt    1622 gttcggcata caaataatac ctatatctta attgtaagca aaactttggg gaaggatga    1682 atagaattca tttgattatt tcttcatgtg tgtttagtat ctgaatttga aactcatctg    1742 gtggaaacca agtttcaggg gacatgagtt ttccagcttt tatacacacg tatctcattt    1802 ttatcaaaac attttgttt                                                  1821
```

<210> SEQ ID NO 2
<211> LENGTH: 476
<212> TYPE: PRT
<213> ORGANISM: Homo sapiens

<400> SEQUENCE: 2

```
Met Ala Val Pro Phe Val Glu Asp Trp Asp Leu Val Gln Thr Leu Gly
  1               5                  10                  15

Glu Gly Ala Tyr Gly Glu Val Gln Leu Ala Val Asn Arg Val Thr Glu
             20                  25                  30

Glu Ala Val Ala Val Lys Ile Val Asp Met Lys Arg Ala Val Asp Cys
         35                  40                  45

Pro Glu Asn Ile Lys Lys Glu Ile Cys Ile Asn Lys Met Leu Asn His
     50                  55                  60

Glu Asn Val Val Lys Phe Tyr Gly His Arg Arg Glu Gly Asn Ile Gln
 65                  70                  75                  80

Tyr Leu Phe Leu Glu Tyr Cys Ser Gly Gly Glu Leu Phe Asp Arg Ile
                 85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270
```

```
Ala Lys Arg Pro Arg Val Thr Ser Gly Gly Val Ser Glu Ser Pro Ser
    275                 280                 285

Gly Phe Ser Lys His Ile Gln Ser Asn Leu Asp Phe Ser Pro Val Asn
    290                 295                 300

Ser Ala Ser Ser Glu Glu Asn Val Lys Tyr Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415

Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
        435                 440                 445

Leu Glu Phe Lys Arg His Phe Leu Lys Ile Lys Gly Lys Leu Ile Asp
    450                 455                 460

Ile Val Ser Ser Gln Lys Val Trp Leu Pro Ala Thr
465                 470                 475

<210> SEQ ID NO 3
<211> LENGTH: 18
<212> TYPE: RNA
<213> ORGANISM: Artificial Sequence
<220> FEATURE:
<223> OTHER INFORMATION: generic RNA
<220> FEATURE:
<221> NAME/KEY: misc_feature
<222> LOCATION: (1)...(18)
<223> OTHER INFORMATION: n = A,U,C or G

<400> SEQUENCE: 3
nnnnnnnnuh nnnnnnnn                                              18

<210> SEQ ID NO 4
<211> LENGTH: 39
<212> TYPE: RNA
<213> ORGANISM: Artificial Sequence
<220> FEATURE:
<223> OTHER INFORMATION: theoretical ribozyme
<220> FEATURE:
<221> NAME/KEY: misc_feature
<222> LOCATION: (1)...(39)
<223> OTHER INFORMATION: n = A,U,C or G

<400> SEQUENCE: 4
nnnnnnnncu gaugagcaug agcaugcgaa annnnnnnn                       39

<210> SEQ ID NO 5
<211> LENGTH: 1821
<212> TYPE: RNA
<213> ORGANISM: Homo sapiens

<400> SEQUENCE: 5
```

```
ggccggacag uccgccgagg ugcucggugg agucauggca gugcccuuug uggaagacug        60
ggacuuggug caaacccugg gagaaggugc cuauggagaa guucaacuug cugugaauag       120
aguaacugaa gaagcagucg cagugaagau uguagauaug aagcgugccg uagacugucc       180
agaaaauauu aagaaagaga ucuguaucaa uaaaaugcua aaucaugaaa auguaguaaa       240
auucuauggu cacaggagag aaggcaauau ccaauauuua uuucuggagu acuguagugg       300
aggagagcuu uuugacagaa uagagccaga cauaggcaug ccugaaccag augcucagag       360
auucuuccau caacucaugg caggggugu uuaucugcau gguauggaa uaacucacag         420
ggauauuaaa ccagaaaauc uucuguugga ugaaagggau aaccucaaaa ucucagacuu       480
uggcuuggca acaguauuuc gguauaauaa ucgugagcgu uuguugaaca agaugugugg       540
uacuuuacca uauguugcuc cagaacuucu gaagagaaga gaauuucaug cagaaccagu       600
ugauguuugg uccuguggaa uaguacuuac ugcaaugcuc gcuggagaau ugccauggga       660
ccaacccagu gacagcuguc aggaguauuc ugacuggaaa gaaaaaaaaa cauaccucaa       720
cccuuggaaa aaaaucgauu cugcuccucu agcucugcug cauaaaaucu uaguugagaa       780
uccaucagca agaauuacca uuccagacau caaaaaagau agauggauaca acaaaccccu      840
caagaaaggg gcaaaaaggc cccgagucac uucagguggu gugucagagu cucccagugg      900
auuuucuaag cacauucaau ccaauuugga cuucucucca guaaacagug cuucuaguga       960
agaaaaugug aaguacucca guucucagcc agaacccccgc acaggucuuu ccuuauggga    1020
uaccagcccc ucauacauug auaaauuggu acaagggauc agcuuuuccc agcccacaug     1080
uccugaucau augcuuuuga auagucaguu acuuggcacc ccaggauccu cacagaaccc     1140
cuggcagcgg uuggucaaaa gaaugacacg auucuuuacc aaauuggaug cagacaaauc     1200
uuaucaaugc cugaaagaga cuugugagaa guugggcuau caauggaaga aaaguuguau     1260
gaaucagguu acuauaucaa caacugauag gagaaacaau aaacucauuu ucaaagugaa     1320
uuuguuagaa auggaugaua aaauauuggu ugacuuccgg cuuucuaagg gugauggauu     1380
ggaguucaag agacacuucc ugaagauuaa agggaagcug auugauauug ugagcagcca     1440
gaagguuugg cuuccugcca caugaucgga ccaucggcuc uggggaaucc uggugaauau     1500
agugcugcua uguugacauu auucuuccua gagaagauua uccuguccug caaacugcaa     1560
auaguaguuc cugaaguguu cacucccug uuuauccaaa caucuuccaa uuuauuuugu      1620
uuguucggca uacaaauaau accuauaucu uaauuguaag caaaacuuug gggaaaggau     1680
gaauagaauu cauuugauua uuucuucaug uguguuuagu aucugaauuu gaaacucauc     1740
ugguggaaac caaguuucag gggacaugag uuuuccagcu uuuauacaca cguaucucau     1800
uuuuaucaaa acauuuuguu u                                                1821
```

Those skilled in the art will recognize, or be able to ascertain using no more than routine experimentation, many equivalents to the specific embodiments of the invention described herein. Such equivalents are intended to be encompassed by the following claims.

What is claimed is:

1. A method for screening compounds to identify candidate compounds for increasing the drug resistance of a cell, the method comprising:

a) determining the level of expression of Chk1 comprising the nucleic acid sequence of SEQ ID NO:1 in a cell in the presence of a selected compound;

b) determining the level of expression of Chk1 comprising the nucleic acid sequence of SEQ ID NO:1 in the cell in the absence of the selected compound; and c) identifying the selected compound as a candidate compound for increasing the drug resistance of the cell if the level of expression of Chk1 comprising the nucleic acid sequence of SEQ ID NO;1 in the cell in the presence of the selected compound is greater than the level of expression of Chk1 comprising the nucleic acid sequence of SEQ ID NO:1 in the cell in the absence of the selected compound.

2. A method for screening compounds to identify candidate compounds for decreasing the drug resistance of a cell, the method comprising:
 a) determining the level of expression of Chk1 comprising the nucleic acid sequence of SEQ ID NO:1 in a cell in the presence of a selected compound;
 b) determinig the level of expression of Chk1 comprising the nucleic acid sequence of SEQ ID NO:1 in the cell in the absence of the selected compound; and
 c) identifying the selected compound as a candidate compound for decreasing the drug resistance of the cell if the level of expression of Chk1 comprising the nucleic acid sequence of SEQ ID NO:1 in the cell in the presence of the selected compound is less than the level of expression of the Chk1 comprising the nucleic acid sequence of SEQ ID NO:1 in the cell in the absence of the compound.

3. The method of claim 1 or 2 wherein Chk1 comprising the nucleic acid sequence of SEQ ID NO:1 is endogenous.

4. The method of claim 1 or 2 wherein the cell is a cancer cell.

5. The method of claim 4 wherein the cancer cell a cultured cell.

6. The method of claim 5 wherein the cultured cancer cell is a UCLA cell.

7. The method of claim 4 wherein the cancer cell is a drug resistant cancer cell.

8. The method of claim 7 wherein the cancer cell is resistant to vinblastine.

9. The method of claim 7 wherein the cell is resistant to adromycin.

10. The method of claim 7 wherein the cancer cell is a breast carcinoma cell.

11. The method of claim 7 wherein the cancer cell is a prostate carcinoma cell.

12. The method of claim 7 wherein the cancer cell is a lung carcinoma cell.

13. The method of claim 1 or 2 wherein expression is determined by measuring the level of an mRNA encoding a polypeptide comprising the amino acid sequence of SEQ ID NO:2.

14. The method of claim 1 or 2 wherein expression is determined by measuring the level of a polypeptide comprising the amino acid sequence of SEQ ID NO:2.

15. The method of claim 1 or 2 wherein expression is measured in the presence of a chemotherapeutic drug.

16. The method of claim 15 wherein the chemotherapeutic drug is selected from the group consisting of doxorubicin, vinblastineand adromycin.

17. The method of claim 1 or 2 wherein the cell is a non-neoplastic cell.

18. A method for screening compounds to indentify compounds that increase the drug resistance of a cell, the method comprising:
 a) determining the level of expression of Chk1 comprising the nucleic acid sequence of SEQ ID NO:1 in a cell in the precence of a selected compound;
 b) determining the level of expression of Chk1 comprising the nucleic acid sequence of SEQ ID NO:1 in the cell in the absence of the selected compound;
 c) identifying the selected compound as a candidate compound for increasing the drug resistance of the cell if the level of expression of Chk1 comprising the nucleic acid sequence of SEQ ID NO:1 in the cell in the presence of the selected compound is greater than the level of expression of Chk1 comprising the nucleic acid sequence of SEQ ID NO:1 in the cell in the absence of the compond;
 d) measuring the resistance of the cell to a selected drug in the presence and absence of a compound identified as a candidate compound; and
 e) identifying the candidate compound as a compound that increases the drug resistance of the cell if the resistance of the cell to the selected drug is increased in the presence of the candidate compound.

19. A method for screening compounds to identify compounds that decrease the drug resistance of a cell, the method comprising:
 a) determining the level of expression of Chk1 comprising the nucleic acid sequence of SEQ ID NO:1 in a cell in the presence of a selected compound;
 b) determining the level of expression of Chk1 comprising the nucleic acid sequence of SEQ ID NO:1 in the cell in the absence of the selected compound;
 c) identifying the selected compound as a candidate compound for decreasing the drug resistance of the cell if the level of expression of Chk1 comprising the nucleic acid sequence of SEQ ID NO:1 in the cell in the presence of the selected compound is less than the level of expression of the Chk1 comprising the nucleic acid sequence of SEQ ID NO:1 in the cell in the absence of the compound;
 d) measuring the resistance of the cell to a selected drug in the presence and absence of a compound identified as a candidate compound; and
 identifying the candidate compound as a compound that decreases the drug resistance of the cell if the resistance of the cell to the selected drug is decreased in the presence of the candidate compound.

20. The method of claim 18 or 19 wherein Chk1 comprising the nucleic acid sequence of SEQ ID NO:1 is encoded by an endogenous gene.

21. The method of claim 18 or 19 wherein the cell is a cancer cell.

22. The method of claim 21 wherein the cancer cell a cultured cell.

23. The method of claim 22 wherein the cultured cancer cell is a UCLA cell.

24. The method of claim 21 wherein the cancer cell is a drug resistant cancer cell.

25. The method of claim 24 wherein the cancer cell is resistant to vinblastine.

26. The method of claim 24 wherein the cell is resistant to adromycin.

27. The method of claim 24 wherein the cancer cell is a breast carcinoma cell.

28. The method of claim 24 wherein the cancer cell is a prostate carcinoma cell.

29. The method of claim 24 wherein the cancer cell is a lung carcinomia cell.

30. The method of claim 18 or 19 wherein expression is determined by measuring the level of an mRNA encoding a polypeptide comprising the amino acid sequence of SEQ ID NO:2.

31. The method of claim 18 or 19 wherein expression is determined by measuring the level of a polypeptide comprising the amino acid sequence of SEQ ID NO:2.

32. The method of claim 18 or 19 wherein expression is measured in the presence of a chemotherapeutic drug.

33. The method of claim 32 wherein the chemotherapeutic drug is selected from the group consisting of doxorubicin, vinblastine, and adromycin.

34. The method of claim 18 or 19 wherein the cell is a non-neoplastic cell.

35. The method of any of of claims 1, 2, 18 or 19 wherein Chk1 comprising the nucleic acid sequence of SEQ ID NO:1 is non-endogenous.

36. The method of any of claims 1, 2, 18 and 19 wherein the polypeptide comprising the amino acid sequence of SEQ ID NO:2 is encoded by an mRNA comprising the nucleotide sequence of SEQ ID NO:1 wherein each T is replaced by a U.

37. The method of claim 13 wherein the mRNA comprises the nucleotide sequence of SEQ ID NO:1 wherein each T is replaced by a U.

38. The method of claim 30 wherein the mRNA comprises the nucleotide sequence of SEQ ID NO:1 wherein each T is replaced by a U.

* * * * *